(12) United States Patent
Miller

(10) Patent No.: US 7,053,213 B2
(45) Date of Patent: *May 30, 2006

(54) THERAPEUTIC HETEROCYCLES

(75) Inventor: Scott Carson Miller, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 355 days.

This patent is subject to a terminal disclaimer.

(21) Appl. No.: 10/233,160

(22) Filed: Aug. 30, 2002

(65) Prior Publication Data

US 2003/0187255 A1    Oct. 2, 2003

Related U.S. Application Data

(62) Division of application No. 09/668,257, filed on Sep. 22, 2000, now Pat. No. 6,444,809, which is a division of application No. 09/336,087, filed on Jun. 18, 1999, now Pat. No. 6,124,279, which is a division of application No. 09/106,606, filed on Jun. 29, 1998, now Pat. No. 5,990,130, which is a division of application No. 08/689,199, filed on Aug. 5, 1996, now Pat. No. 5,861,392, which is a division of application No. 08/290,642, filed on Aug. 15, 1994, now Pat. No. 5,567,700.

(30) Foreign Application Priority Data

Aug. 17, 1993    (GB) .................................... 9317104

(51) Int. Cl.
- C07D 413/04    (2006.01)
- C07D 239/02    (2006.01)
- C07D 419/04    (2006.01)

(52) U.S. Cl. .................. 544/96; 544/317; 546/209; 546/210

(58) Field of Classification Search .............. 544/96, 544/317; 546/209, 210
See application file for complete search history.

(56) References Cited

U.S. PATENT DOCUMENTS

| 5,236,921 | A |   | 8/1993  | Emonds-Alt et al. | 514/252    |
|-----------|---|---|---------|-------------------|------------|
| 5,559,131 | A |   | 9/1996  | Miller            | 514/329    |
| 5,559,132 | A |   | 9/1996  | Miller            | 514/329    |
| 5,567,700 | A | * | 10/1996 | Miller            | 514/226.8  |
| 5,576,333 | A |   | 11/1996 | Miller            | 514/316    |
| 5,602,138 | A |   | 2/1997  | Miller            | 514/259    |
| 5,861,392 | A | * | 1/1999  | Miller            | 514/212.08 |
| 5,990,130 | A | * | 11/1999 | Miller            | 514/326    |
| 6,444,809 | B1| * | 9/2002  | Miller            | 540/488    |

FOREIGN PATENT DOCUMENTS

| CA | 2029275    | 5/1991  |
| CA | 2067924    | 11/1992 |
| CA | 2090785    | 9/1993  |
| EP | 0428434    | 5/1991  |
| EP | 0474561    | 3/1992  |
| EP | 0512901    | 11/1992 |
| EP | 0512902    | 11/1992 |
| EP | 0515240    | 11/1992 |
| EP | 0515250    | 11/1992 |
| EP | 0559538    | 9/1993  |
| WO | WO 91/09844| 7/1991  |
| WO | WO 94/10146| 5/1994  |
| ZA | 923177     | 1/1993  |
| ZA | 923178     | 1/1993  |

OTHER PUBLICATIONS

A. Graham et al., "Isolaton and Characterisation of the Human Lung NK-2 Receptor Gene Using Rapid Amplification of cDNA Ends", *Biochemical and Biophysical Research Communications*, (1991), vol. 177, No. 1, 8-16.

X. Emonds-Alt et al., "Pharmacological Profile and Chemical Synthesis of SR 48968, a Non-Peptide Antagonist of the Neurokinin A (NK2) Receptor", *Biorganic & Medicinal Chemistry Letters*, (1993), vol. 3, No. 5, 925-930.

D. Aharony et al., "Pharmacologic Characterization of the Novel Ligand [4, 5-3H-LEU9] Neurokinin-A Binding to NK-2 Receptors on Hamster Urinary Bladder Membranes", *Neuropeptides*, (1992), 23, 121-130.

M. Needham et al., "LCR/MEL: A Versatile System for High-Level Expression of Heterologous Proteins in Erythroid Cells", *Nucleic Acids Research*, (1992), vol. 20, No. 5, 997-1003.

* cited by examiner

*Primary Examiner*—Peter O'Sullivan
(74) *Attorney, Agent, or Firm*—Kenneth F. Mitchell

(57) ABSTRACT

Pharmaceutical compositions containing novel therapeutic heterocycles for use in diseases in which an NK2 receptor is implicated, processes for preparing and methods for using the same.

3 Claims, 3 Drawing Sheets

THERAPEUTIC HETEROCYCLES

This is a divisional of application Ser. No. 09/668,257, filed Sep. 22, 2000, now U.S. Pat. No. 6,444,809, which is a Divisional of application Ser. No. 09/336,087 filed Jun. 18, 1999, now U.S. Pat. No. 6,124,279, which is a divisional of application Ser. No. 09/106,606 filed Jun. 29, 1998, now U.S. Pat. No. 5,990,130, which is a divisional of application Ser. No. 08/689,199 filed Aug. 5, 1996, now U.S. Pat. No. 5,861,392, which is a divisional of parent application Ser. No. 08/290,642 filed Aug. 15, 1994, now U.S. Pat. No. 5,567,700.

This invention concerns novel therapeutic heterocycles, and, more particularly, novel 4-substituted piperidine derivatives which antagonize the pharmacological actions of one of the endogenous neuropeptide tachykinins known as neurokinins, particularly at the neurokinin 2 (NK2) receptor. The novel therapeutic heterocycles are useful whenever such antagonism is desired. Thus, such compounds may be of value in the treatment of those diseases in which an NK2 receptor is implicated, for example, in the treatment of asthma and related conditions. The invention also provides pharmaceutical compositions containing the novel therapeutic heterocycles for use in such treatment, methods for their use, and processes and intermediates for the manufacture of the novel therapeutic heterocycles.

The mammalian neurokinins comprise a class of peptide neurotransmitters which are found in the peripheral and central nervous systems. The three principal neurokinins are Substance P (SP), Neurokinin A (NKA) and Neurokinin B (NKB). There are also N-terminally extended forms of at least NKA. At least three receptor types are known for the three principal neurokinins. Based upon their relative selectivities favoring the neurokinin agonists SP, NKA and NKB, respectively, the receptors are classified as neurokinin 1 (NK1), neurokinin 2 (NK2) and neurokinin 3 (NK3) receptors, respectively. In the periphery, SP and NKA are localized in C-afferent sensory neurons, which neurons are characterized by non-myelinated nerve endings known as C-fibers, and are released by selective depolarization of these neurons, or selective stimulation of the C-fibers. C-Fibers are located in the airway epithelium, and the tachykinins are known to cause profound effects which clearly parallel many of the symptoms observed in asthmatics. The effects of release or introduction of tachykinins in mammalian airways include bronchoconstriction, increased microvascular permeability, vasodilation and activation of mast cells. Thus, the tachykinins are implicated in the pathophysiology and the airway hyperresponsiveness observed in asthmatics; and blockade of the action of released tachykinins may be useful in the treatment of asthma and related conditions.

Peptidic NK2 antagonists have been reported. For example, a cyclic hexapeptide known as L-659,877 has been reported as a selective NK2 antagonist. Nonpeptidic NK2 antagonists also have been reported, for example, certain piperidines are disclosed in European Patent Applications, Publication Nos. 428434, 474561, 512901, 512902, 515240, and 559538. A series of piperidine NK2 antagonists has also been reported in International Application, Publication No. WO 94/10146.

We have discovered a series of novel nonpeptidic NK2 antagonists and this is the basis for our invention. One aspect of the discovery includes 4-substituted piperidine derivatives in which the 4-substituent is an N-linked heterocycle (as defined below). For example, we discovered the 4-(2-oxo-1,3-oxazolidin-3-yl)piperidino compound disclosed below at Example 1 to be a potent NK2 antagonist in the in vitro screen described below as Test A and in the functional assay described below as Test B.

According to the invention, there is provided a Compound of the invention; which is a compound of formula I (formula set out hereinbelow following the Examples, together with other formulae denoted by Roman numerals) wherein m is 2 or 3;

D is a residue of formula Ia or formula Ib wherein

Q is phenyl which may bear one or two substituents independently selected from halo, trifluoromethyl, hydroxy, (1–3C)alkoxy, (1–3C)alkyl and methylenedioxy; or Q is thienyl, imidazolyl, benzo[b]thiophenyl or naphthyl any of which may bear a halo substituent; or Q is biphenylyl; or Q is carbon-linked indolyl which may bear a benzyl substituent at the 1-position;

$Q^a$ is hydrogen, (1–4C)alkyl, or a radical of formula $-(CH_2)_q-NR^5R^6$ in which q is 2 or 3 and $R^5$ and $R^6$ are independently (1–4C)alkyl or $NR^5R^6$ is piperidino or 4-benzylpiperidino;

$R^1$ is hydrogen, methyl or (2–6C)n-alkyl which may bear a terminal amino radical;

$R^2$ is $-C(=O)R^3$, $-C(=O)OR^3$ or $-C(=J^1)NHR^3$ in which $J^1$ is oxygen or sulfur and $R^3$ is hydrogen, (1–6C)alkyl, phenyl(1–3C)alkyl (in which the phenyl may bear one more halo, hydroxy, (1–4C)alkoxy or (1–4C)alkyl substituents), pyridyl(1–3C)alkyl, naphthyl(1–3C)alkyl, pyridylthio (1–3C)alkyl, styryl, 1-methylimidazol-2-ylthio(1–3C)alkyl, aryl (which may bear one or more halo, hydroxy, (1–4C) alkoxy or (1–4C)alkyl substituents), heteroaryl (which may bear one or more halo, hydroxy, (1–4C)alkoxy or (1–4C) alkyl substituents), or (when $R^2$ is $-COR^3$)α-hydroxybenzyl;

n is 0, 1, 2 or 3;

p is 1 or 2, and when p is 2, n is 1 and $J^2$ is two hydrogens;

$J^2$ is oxygen or two hydrogens;

$L^6$ is carbonyl or methylene;

r is 0, 1, 2, or 3; and $R^4$ is phenyl which may bear one or more halo, trifluoromethyl, (1–4C)alkyl, hydroxy or (1–4C)alkoxy substituents (and particularly one or more chloro or fluoro substituents); naphthyl which may bear one or more halo, trifluoromethyl, (1–4C)alkyl or hydroxy substituents; pyridyl; thienyl; indolyl; quinolinyl; benzothienyl or imidazolyl; or when $L^6$ is carbonyl, the group $-(CH_2)_r-R^4$ may represent aryl, heteroaryl or a benzyl group bearing an α-substituent selected from hydroxy, (1–4C)alkoxy and (1–4)alkyl, and further wherein the aryl, heteroaryl or phenyl portion of the benzyl group may bear one or more substituents selected independently from halo, trifluoromethyl, (1–4C)alkyl, hydroxy and (1–4C)alkyl, hydroxy and (1–4C)alkoxy (and particularly one or more chloro or fluoro substituents);

G denotes a single bond, a double bond or a divalent hydrocarbon radical;

J denotes a radical joined to the ring by a single bond if G denotes a double bond or, otherwise, a radical joined by a double bond;

M denotes a heteroatom or substituted heteroatom; and

L denotes a hydrocarbon radical in which the 1-position is attached to M; wherein the values of G, J, M and L are selected from (a) G is a single bond; J is oxo or thioxo; M is oxy, thio or $NR^{12}$; and L is $L^1$;

(b) G is a single bond; J is $NR^8$; M is $NR^7$; and L is $L^1$;

(c) G is a double bond, J is $OR^7$, $SR^7$ or $NR^9R^{10}$; M is nitrogen; and L is $L^1$;

(d) G is methylene which may bear one or two methyl substituents; J is oxo, thio or $NR^{11}$; M is oxy, thio, sulfinyl, sulfonyl or $NR^7$; and L is $L^2$;

(e) G is a single bond; J is oxo, thioxo or $NR^{11}$; M is nitrogen; and L is $L^3$;

(f) G is methine, which may bear a (1–3C)alkyl substituent; J is oxo, thioxo or $NR^{11}$; M is nitrogen; and L is $L^4$; and (g) G is cis-vinylene, which may bear one or two methyl substituents; J is oxo, hioxo, or $NR^{11}$; M is nitrogen; and L is $L^5$; wherein $R^7$ is hydrogen or (1–3C)alkyl;

$R^8$ is hydrogen, (1–3C)alkyl, cyano, (1–3C)alkylsulfonyl or nitro;

$R^9$ and $R^{10}$ are independently hydrogen or (1–3C)alkyl or the radical $NR^9R^{10}$ is pyrrolidino, piperidino, morpholino, thiomorpholino (or its S-oxide) or piperazino (which may bear a (1–3C)alkyl substituent at the 4-position);

$R^{11}$ is hydrogen or (1–3C)alkyl;

$R^{12}$ is hydrogen, (1–3C)alkyl, RaOC(=O)CH$_2$— or RbRcNC(=O)CH$_2$—.

$R^a$ is hydrogen or (1–3C)alkyl;

$R^b$ and Rc are independently hydrogen, (1–3C)alkyl, phenyl or benzyl;

$L^1$ is ethylene, cis-vinylene, trimethylene or tetramethylene which radical $L^1$ itself may bear one or two methyl substituents;

$L^2$ is ethylene or trimethylene which radical $L^2$ itself may bear one or two methyl substituents;

$L^3$ is prop-2-en-1-yliden-3-yl, which radical $L^3$ itself may bear one or two methyl substituents;

$L^4$ is cis-vinylene, which radical $L^4$ itself may bear one or two methyl substituents; and $L^5$ is methine, which radical $L^5$ itself may bear a (1–3C) alkyl substituent;

or the N-oxide of said compound of formula I at the piperidino nitrogen indicated by Δ;

or a pharmaceutically acceptable salt of said compound of formula I or said N-oxide;

or a quaternary ammonium salt of said compound of formula I in which the piperidino nitrogen indicated by Δ is a quadricovalent ammonium nitrogen wherein the fourth radical on the nitrogen is (1–4C)alkyl or benzyl and the associated counterion is a pharmaceutically acceptable anion.

It will be appreciated that a compound of formula I contains one or more asymmetrically substituted carbon atoms such that such a compound may be isolated in optically active, racemic and/or diastereomeric forms. It will further be appreciated that a compound of formula I may exist in tautomeric forms and that a compound may exhibit polymorphism. It is to be understood that the present invention encompasses any racemic, optically-active, diastereomeric, tautomeric, polymorphic or stereoisomeric form, or mixture thereof, which form possesses NK2 antagonist properties, it being well known in the art how to prepare optically-active forms (for example, by resolution of the racemic form or by synthesis from optically-active starting materials) and how to determine the NK2 antagonist properties by the standard tests described hereinafter. It may be preferred to use the compound of formula I in a form which is characterized as containing, for example, at least 95%, 98% or 99% enantiomeric excess. Further, it may be preferred to use a compound of formula I, which is a compound of formula Ic, in a form which is characterized as containing, for example, at least 95%, 98% or 99% enantiomeric excess of the form with the (S)-configuration at the center indicated by * in the formula.

In this specification $R^a$, $R^b$, $R^1$, $R^2$, et cetera stand for generic radicals and have no other significance. It is to be understood that the generic term "(1–3C)alkyl" includes both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, alkoxy, alkanoyl, et cetera. Halo is fluoro, chloro, bromo or iodo.

Particular values are listed below for radicals, substituents and ranges for Compounds for illustration only and they do not exclude other defined values or other values within defined ranges for the radicals and substituents.

A particular value for m is 2.

A particular value for (1–6C)alkyl is methyl, ethyl, propyl, isopropyl or butyl.

A particular value for (1–3C)alkyl is methyl or ethyl.

When D is formula Ia, a particular value for $Q^a$ is hydrogen, a particular value for $R^1$ is methyl and a particular value for $R^2$ is —$COR^3$. A particular value for $R^3$ is aryl, and more particularly phenyl, which aryl (or phenyl) may bear one or two chloro or fluoro substituents.

When D is formula Ib, a particular value for n is 1 or 2; a particular value for p is 1; a particular value for $J^2$ is two hydrogens; a particular value for $L^6$ is carbonyl; a particular value for r is 0 or 1; and a particular value for $R^4$ is phenyl which may bear one or two halo or (1–4C)alkoxy substituents, and more particularly a chloro, fluoro or isopropoxy substituent.

A particular value for Q is, for example, phenyl which may bear one or two substituents selected from halo, trifluoromethyl and methylenedioxy; and, more particularly, 3,4-dichlorophenyl or 3,4-methylenedioxyphenyl.

A particular value for G is, for example, a single bond or methylene; and, more particularly, a single bond. A particular value for J is, for example, oxo, thioxo, imino, methylimino or ethylimino; and, more particularly, oxo or thioxo. A particular value for M is oxy, thio or NH; and, more particularly, oxy or NH. A particular value for L is, for example ethylene, cis-vinylene or trimethylene; and, more particularly, ethylene or trimethylene.

A particular group of compounds of formula I are compounds of formula Ic wherein: $Q^b$ is phenyl which may bear one or two substituents independently selected from halo, trifluoromethyl, hydroxy, (1–3C)alkoxy, (1–3C)alkyl and methylenedioxy; or $Q^b$ is thienyl, imidazolyl, benzo[b]thiophenyl or naphthyl any of which may bear a halo substituent; or $Q^b$ is biphenylyl; or $Q^b$ is carbon-linked indolyl which may bear a benzyl substituent at the 1-position; T and U are independently hydrogen, halo, hydroxy, (1–3C)alkyl or (1–3C)alkoxy; W is (1–3C) alkyl; and G, J, L and M have any of the meanings defined for the corresponding radical in a compound of formula I; or the N-oxide of said compound of formula I at the piperidino nitrogen indicated by Δ; or a pharmaceutically acceptable salt of said compound of formula I or said N-oxide; or a quaternary ammonium salt of said compound of formula I in which the piperidino nitrogen indicated by Δ is a quadricovalent ammonium nitrogen wherein the fourth radical on the nitrogen is (1–4C)alkyl or benzyl and the associated counterion is a pharmaceutically acceptable anion.

Another particular group of compounds of formula I are compounds of formula Ic wherein: $R^{12}$ is hydrogen or (1–3C)alkyl; T and U are hydrogen; and W is methyl; and pharmaceutically acceptable salts thereof.

Preferred compounds include (S)-N-[2-(3,4- dichlorophenyl)-4-[4-(2-oxoperhydropyrimidin-1- yl)piperidino]butyl]-N-methylbenzamide;

(S)-N-[2-(3,4-dichlorophenyl)-4-[4-(3-methyl-2- oxoperhy- dropyrimidin-1-yl)piperidino]butyl]-N-methylbenzamide;

(S)-N-[2-(3,4-dichlorophenyl)-4-[4-(3-ethyl-2-oxoperhydropyrimidin-1-yl)-piperidino]butyl]-N-methylbenzamide; and (S)-N-[2-(3,4-dichlorophenyl)-4-[4-(2-oxoperhydropyrimidin-1-yl)-piperidino]butyl]-N-ethylbenzamide; and pharmaceutically acceptable salts thereof.

Specific Compounds are described in the accompanying Examples.

A pharmaceutically acceptable salt is one made with an acid which provides a physiologically acceptable anion. Pharmaceutically acceptable salts include those made with a strong inorganic or organic acid which affords a physiologically acceptable anion, such as, for example, hydrochloric, sulfuric, phosphoric, methanesulfonic, or p-toluenesulfonic acid.

A Compound may be made by processes which include processes known in the chemical art for the production of structurally analogous heterocyclic compounds. Such processes and intermediates for the manufacture of a compound of formula I; or the N-oxide of said compound of formula I at the piperidino nitrogen indicated by Δ; or a pharmaceutically acceptable salt of said compound of formula I or said N-oxide; or a quaternary ammonium salt of said compound of formula I in which the piperidino nitrogen indicated by Δ is a quadricovalent ammonium nitrogen wherein the fourth radical on the nitrogen is (1–4C)alkyl or benzyl and the associated counterion is a pharmaceutically acceptable anion; as defined above, are provided as further features of the invention and are illustrated by the following procedures in which the meanings of generic radicals are as defined above unless otherwise indicated:

(a) Alkylating a piperidine of formula II with an aldehyde of formula IV, by reductive alkylation, or with an alkylating agent of formula V in which Y is a leaving group. Typical values for a leaving group Y include, for example, iodide, bromide, methanesulfonate, p-toluenesulfonate, trifluoromethanesulfonate, and the like. The alkylation is preferably carried out by a conventional reductive alkylation, for example as described in Example 1, by the in situ, acid-catalyzed formation of an imminium salt, followed by reduction with sodium cyanoborohydride in alcoholic solvent.

(b) For a compound of formula I in which G is a single bond; J is oxo or thioxo, respectively; M is oxy, thio or $NR^{12}$; and L is $L^1$; cyclizing a corresponding compound of formula III with a diactivated derivative of carbonic acid or a diactivated thiocarbonyl derivative, respectively. Diactivated derivatives of carbonic acid include, for example, 1,1'-carbonyldiimidazole, chloroformate esters (such as the methyl, ethyl or phenyl ester) and carbonate diesters, as well as phosgene, diphosgene and triphosgene; and diactivated thiocarbonyl derivatives include, for example, 1,1'-thiocarbonyldi-2(1H)-pyridone, 1,1'-thiocarbonyldiimidazole, phenyl chlorodithioformate and thiophosgene. Conveniently, the cyclization is carried in an inert solvent, for example chloroform, tetrahydrofuran or toluene, at a temperature from about ambient temperature to the reflux temperature of the reaction mixture, for example as described in Example 3. If the diactivated derivative of carbonic acid or the diactivated thiocarbonyl derivative is an acid chloride, it may be preferred to add a base, such as for example triethylamine, to the cyclization as an acid acceptor.

(c) For a compound of formula I which is a compound of formula Ic; reacting an amine of formula VIII with a suitable acid chloride. The reaction may be carried out in an inert solvent, such as for example, tetrahydrofuran, diethyl ether, toluene, chloroform or dichloromethane, at a temperature in the range of −78 to 100° C., preferably in the range of −20 to 50° C. The reaction may be carried out, for example, under conditions similar to those described in Example 17.

(d) For a compound of formula I which is a compound of formula Ic; reacting an amine of formula VIII with an activated carboxylic acid derivative. The reaction may be carried out in an inert solvent, such as for example, tetrahydrofuran, diethyl ether, toluene, chloroform or dichloromethane, at a temperature in the range of −78 to 100° C., preferably in the range of −20 to 50° C., in the presence of a suitable activating agent, for example, 1-(3-dimethylaminopropyl)-3-ethylcarbodiimide hydrochloride. The reaction may be carried out, for example, under conditions similar to those described in Example 20.

(e) For an N-oxide of a compound of formula I at the piperidino nitrogen indicated by Δ, oxidizing the piperidino nitrogen indicated by Δ of a compound of formula I using a conventional procedure, such as, for example, using hydrogen peroxide in methanol, peracetic acid, 3-chloroperoxybenzoic acid in an inert solvent (such as dichloromethane) or dioxirane in acetone. Suitable conditions, for example, are described in Example 21.

(f) For a compound of formula I wherein $R^{12}$ is (1–3C) alkyl, RaOC(=O)CH$_2$— or RbRcNC(=O)CH$_2$—, alkylating a corresponding compound of formula I wherein $R^{12}$ is hydrogen with a suitable corresponding alkylating agent. The alkylation may be carried out in an inert solvent, such as for example, tetrahydrofuran, diethyl ether, toluene or 1,2-dimethoxyethane, at a temperature in the range of −78 to 100° C., preferably in the range of 0–50° C., in the presence of a suitable base. Suitable conditions, for example, are described in Example 22.

(g) For a quaternary ammonium salt of a compound of formula I, alkylating the piperidino nitrogen indicated by Δ of the compound of formula I with a suitable alkylating agent. The alkylation may be carried out in an inert solvent, such as for example, tetrahydrofuran, diethyl ether, toluene or 1,2-dimethoxyethane, at a temperature in the range of −78 to 100° C., preferably in the range of 0–50° C., in the presence of a suitable base.

It may be desired to optionally use a protecting group during all or portions of the above described processes; the protecting group then may be removed when the final compound is to be formed.

Whereafter, for any of the above procedures, when a pharmaceutically acceptable salt of a compound of formula I or a pharmaceutically acceptable salt of an N-oxide of a compound of formula I is required, it may be obtained by reacting the corresponding compound of formula I or N-oxide with an acid affording a physiologically acceptable counterion or by any other conventional procedure.

It will also be appreciated that certain of the various optional substituents in the Compounds may be introduced by standard aromatic substitution reactions or generated by conventional functional group modifications either prior to or immediately following the processes above, and as such are included in the process aspect of the invention. Such reactions and modifications include, for example, introduction of nitro or halogeno and reduction of nitro. The reagents and reaction conditions for such procedures are well known in the chemical art.

If not commercially available, the necessary starting materials for the above procedures may be made by procedures which are selected from standard techniques of heterocyclic chemistry, techniques which are analogous to the synthesis of known, structurally similar compounds, and techniques which are analogous to the above described procedures or the procedures described in the Examples. The starting materials and the procedures for their preparation are additional aspects of the invention.

A convenient intermediate for preparation of starting materials of formulae III, IV, and V is an alcohol of formula VI (or VIc). The preparation of an alcohol of formula VIc in which $Q^b$ is 3,4-dichlorophenyl is described in Example 1, parts a)–f); and the preparation of the corresponding optically-active alcohol is described in Example 2, parts a)–e). An alcohol of formula VI may then be oxidized to an aldehyde of formula IV, for example using oxalyl chloride, dimethyl sulfoxide and triethylamine as described in Example 1.g) or using Dess-Martin periodinane (1,1,1-triacetoxy-1,1-dihydro-1,2-benziodoxol-3(1H)-one) as described in Example 2.f); or it may be converted into an alkylating agent of formula V by a conventional procedure. An aldehyde of formula IV may be converted into the corresponding amine of formula III employing a procedure similar to that described in Example 3, parts a)–e). Using a procedure similar to that described in Example 1, an aldehyde of formula IV may be converted into a piperidone of formula VII; and an amine of formula m may be obtained by reductive alkylation of an amine of formula HM-L-NH$_2$ using the piperidone of formula VII and an analogous procedure to one described in Example 1.h) or Example 3, parts a)–e).

For the preparation of a starting material piperidine of formula II, a 1-protected 4-piperidone may be used for a reductive alkylation, followed by a cyclization similar to that described above in procedure (b), and finally deprotection, for example as described in Example 1, parts h)–j). Generally, a starting material piperidine of formula II may be obtained from a 1-protected 4-aminopiperidine or a 1-protected 4-piperidone using conventional synthetic methodology.

As will be clear to one skilled in the art, a variety of sequences is available for preparation of the starting materials, and the sequences leading to the starting materials and products of the invention may be altered if appropriate considerations regarding the synthetic methods and radicals present are followed.

The utility of a Compound may be demonstrated by standard tests and clinical studies, including those described below.

Neurokinin A (NKA) Receptor-Binding Assay (Test A)

The ability of a Compound to antagonize the binding of NKA at the NK2 receptor may be demonstrated using an assay using the human NK2 receptor expressed in Mouse Erythroleukemia (MEL) cells by using MEL cell membranes (MELM) which bear high-affinity and selective NK2 receptors and which is carried out as follows.

BRIEF DESCRIPTION OF THE FIGURES

MEL Cell Expression of Human NK2 Receptor (hNK2R): Heterologous protein expression in Mouse Erythroleukemia (MEL) cells uses the human globin locus control region (LCR) (F. Grosveld et al., Cell (1987) 51, 975–985). The cDNAs are inserted between the human beta-globin promoter and the second intron of the human beta-globin gene, and this expression cassette is then placed downstream of the LCR and transfected into MEL cells (M. Needham et al., Nucl. Acids Res. (1992) 20, 997–1003). Human NK2 receptor cDNA (A. Graham et al., Biochem. Biophys. Res. Commun. (1991) 177, 8–16) was isolated from human lung RNA by polymerase chain reaction and DNA sequenced. Human NK2 receptor cDNA was subcloned into a shuttle vector (pMEG3) containing the beta-globin promoter and the 3' portion of the human beta-globin gene (FIG. 1). Human NK2 receptor cDNA was restricted with Eco 0109 (5' end) and Bam HI (3' end). An oligonucleotide linker-adaptor containing an internal Hind III site and a 3' end Eco 0109 site was ligated to the hNK2R cDNA fragment. The sequence of the top strand oligonucleotide=5'd(GCGCAAGCT-TATGGG) (SEQ ID NO:1) and the bottom strand oligonucleotide=5'd(GTCCCCATAAGCTTGCGC) (SEQ ID NO:2). These were annealed and ligated to the hNK2R fragment by standard methods. Following cleavage with Hind III, the resulting fragment was cloned into the Hind III and Bam HI sites in the polylinker of the shuttle vector pMEG3. The construct (pMEG3/hNK2R) was verified by restriction mapping and sequencing the 5' end and 3' end junctions of cDNA/vector. This was then transformed into E.coli DH5 alpha, and plasmid DNA was isolated by standard methods and verified by restriction mapping and DNA sequencing. A ClaI/Asp718 cassette carrying the beta-globin promoter, human NK2 receptor cDNA and the 3'beta-globin gene fragment was excised and subcloned downstream of the LCR in plasmid pGSE1417 (FIG. 2). The pMEG3/hKNK-2R construct was cleaved with ClaI and Asp718 and cloned directly into the ClaI and Asp718 sites (3' of LCR) in the expression vector GSE1417. The construct GSE1417/hNK2R (13.9 kb) was verified by restriction mapping. E.coli DH5 alpha was transformed and recombinant plasmids verified by restriction mapping. MEL C88 cells (A. Deisseroth et al., Cell (1978) 15, 55–63) were electroporated (M. Antoniou, Methods Molecular Biology (1991) 7, 421–434) with PvuI linearized pGSE1417/human NK2 receptor DNA. Directly after transfection, cells were diluted in culture medium to $10^4$ and $10^5$ cell per mL and 1 mL aliquots transferred to each well of a 24-well plate. G418 was added to a concentration of 1 mg/mL 24 hours after the transfection to select for stable transfectants. Individual clones were picked or pooled to generate populations seven to ten days after the addition of selective medium. FIG. 3 shows the strategy used to isolate transfected MEL/human NK2 receptor cell line. For expression studies, cells were maintained in exponential growth for a period of four days, and then dimethyl sulfoxide (DMSO) was added to a final concentration of 2% (v/v) to induce differentiation and hence expression. Samples were taken 4 days post induction for mRNA and NKA binding analyses. The results indicated that clone #1 expresses hNK2R at the highest level (both hNK2R mRNA and specific NKA binding). This clone was scaled up and is now routinely fermented at 20 litre scale per month and supplied for use in Test A.

Figure 1:
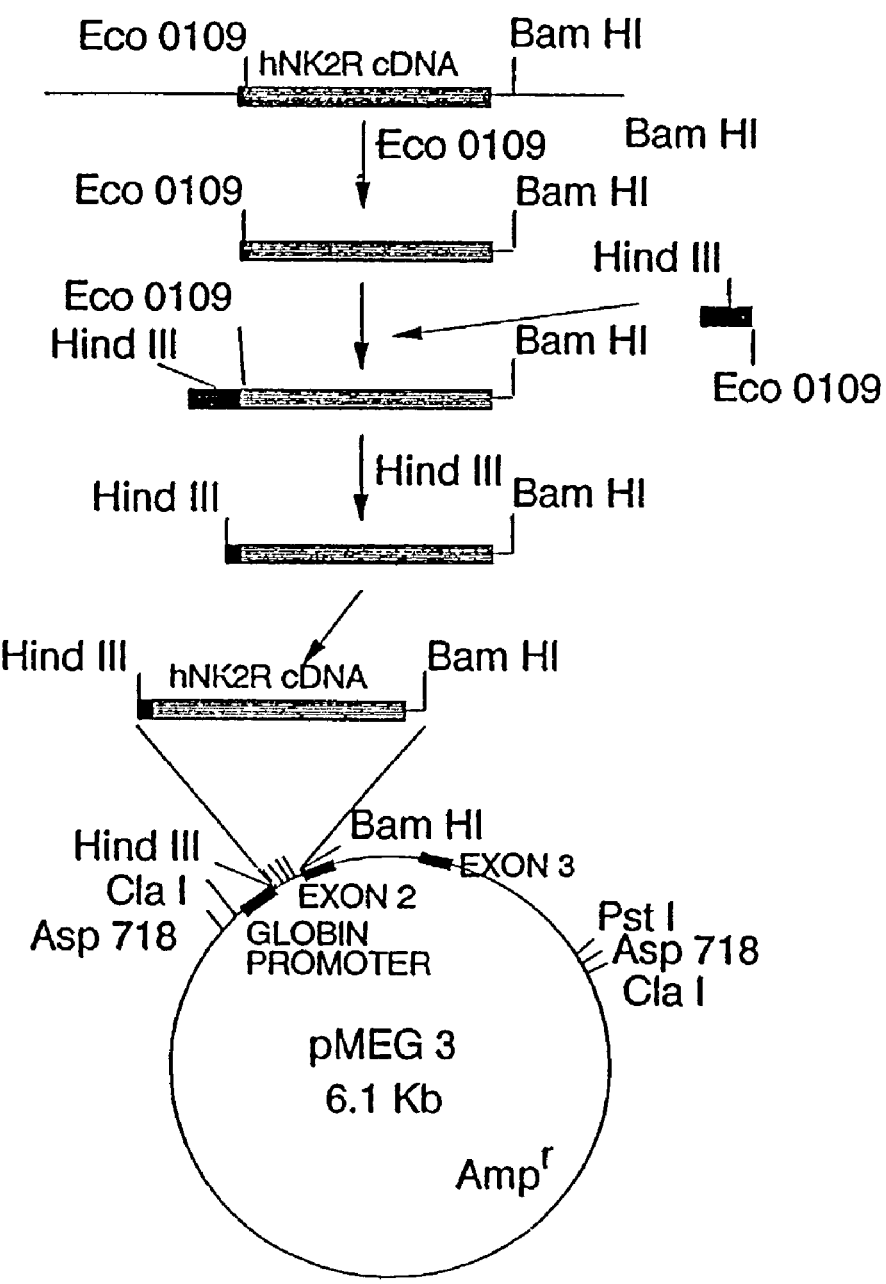
FIG. 1 shows construction of the MEL cell expression vector construct pMEG3/hNK2R.
Figure 2:
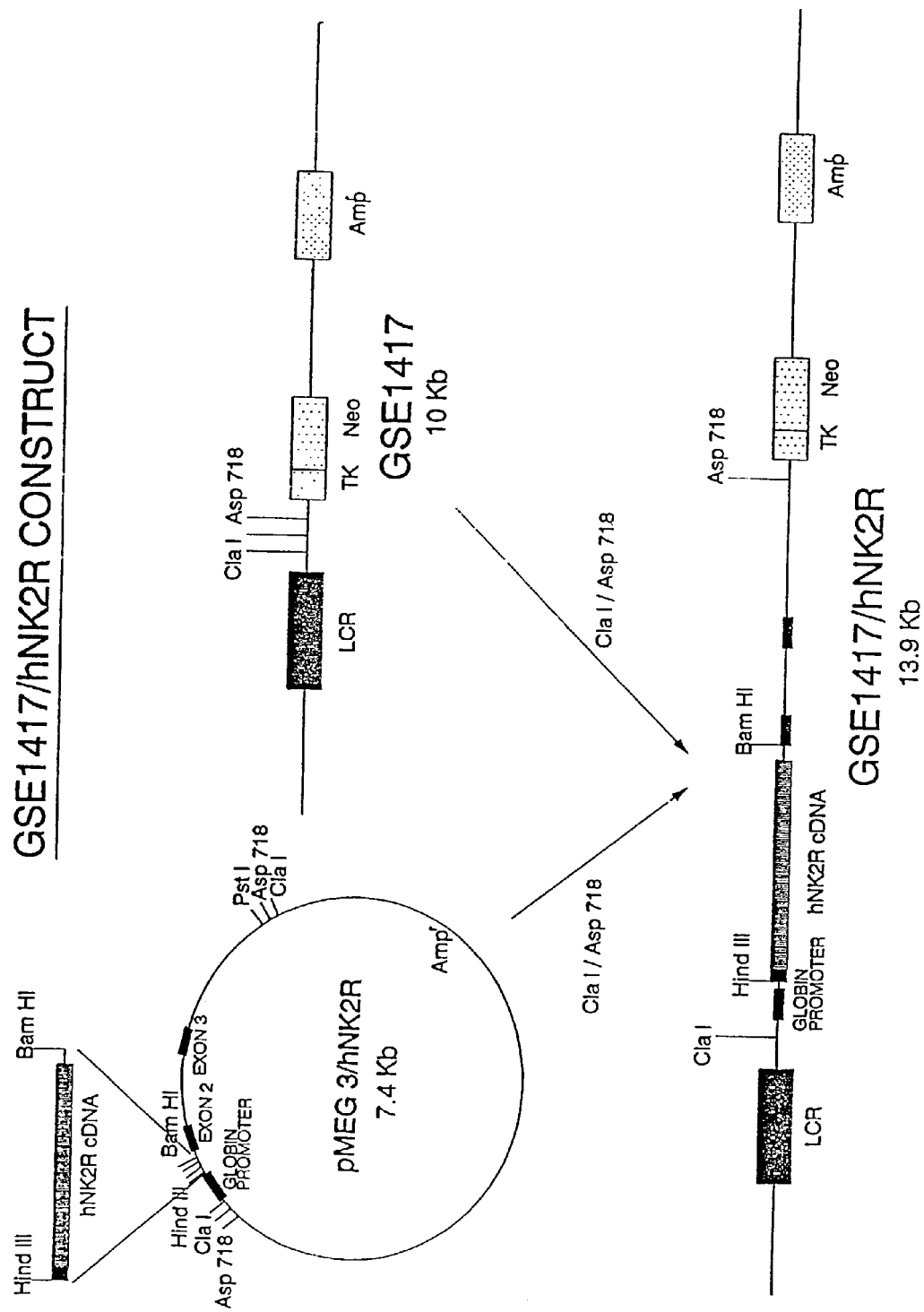
FIG. 2 shows construction of the expression vector construct GSE1417/hNK2R.
Figure 3:
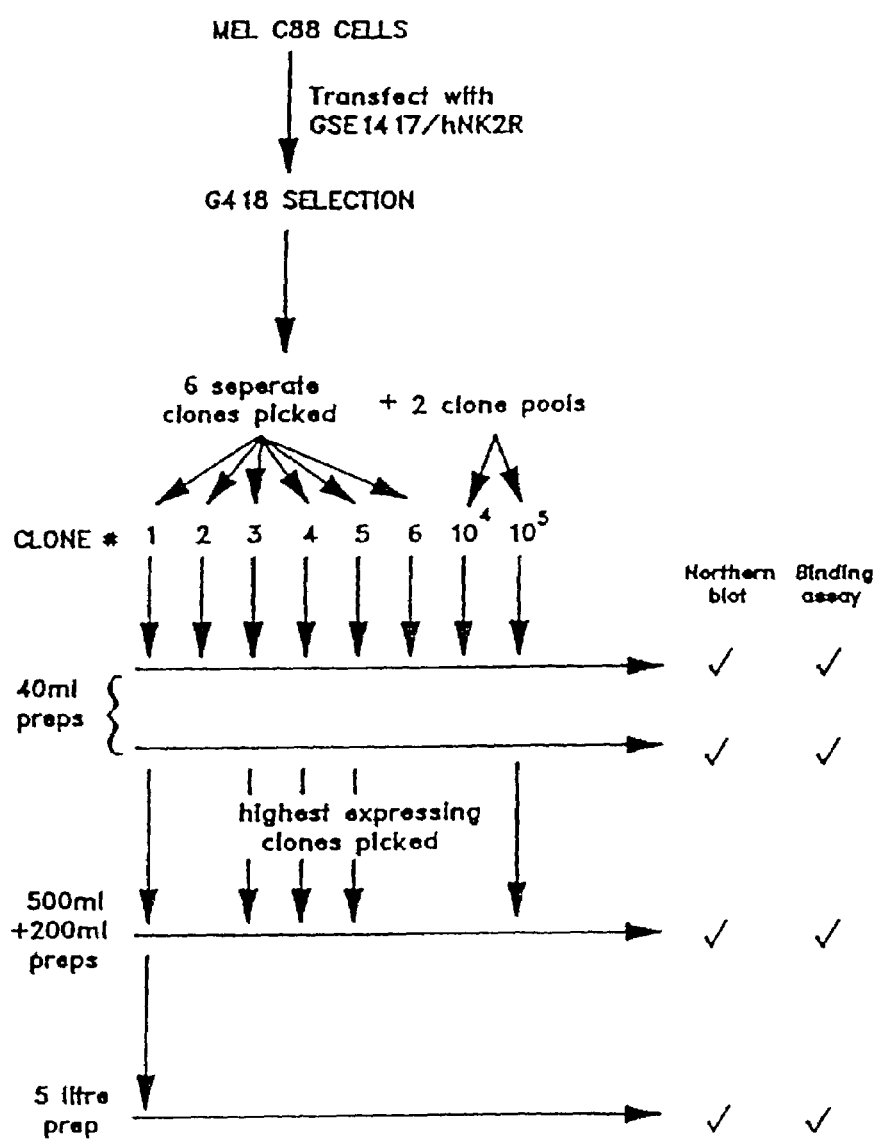
FIG. 3 shows expression of human NK2 receptor in MEL C88 cells.

Membrane preparations (MELM) prepared from the MEL cells containing high-affinity NK2 receptors were prepared according to a published protocol (D. Aharony, et al., Neuropeptides (1992) 23, 121–130) with the following minor modifications: (1) Iodoacetamide (1 mM) was included in the homogenization buffer; (2) Homogenization was as published but for a shorter period of 10 seconds once and at a slower speed (setting 10); and (3) The equilibration step with KCl/EDTA was not performed. In a typical preparation, binding of $^3$H-NKA (2.5 nM) to MELM was highly specific (88±4%) and linearly dependent on the protein concentration, with significant binding detected as low as 26 μg protein/mL. Equilibrium-competion experiments demonstated binding to high-affinity, high-density receptors with $K_D$=1187 nM, $B_{max}$=2229 fmol/mg protein.

The radio ligand $^3$H-neurokinin A ($^3$H-NKA) as [4,5-$^3$H-Leu$^9$]-NKA (typical specific activity, 117 Ci/mmol) is obtained by custom synthesis from Cambridge Research Biochemicals and is >95% pure. Repeated HPLC analysis demonstrated that the ligand is stable under proper storage conditions (silanized vials with 0.2% mercaptoethanol, under argon). Also, no degradation or metabolism is apparent in the receptor-binding assay.

The assay is carried out using an incubation buffer consisting of 50 mM Tris HCl (pH 7.4), 5 mM $Mg^{++}$, 100 μM thiorphan, 1 nM $^3$H-NKA, 0.02% (w:v) BSA, 30 mM $K^+$, and 300 μM dithiothreitol; and the concentration of membrane protein is held at approximately 0.05–0.025 mg per tube. Nonspecific binding is routinely defined with 1 μM NKA. Each tube receives the following: 150 μL incubation buffer, 20 μL $^3$H-NKA, 20 μL Compound, NKA or buffer as appropriate, and 125 μL membrane suspension. The reaction is initiated by the addition of the membranes. The tubes are incubated for 60 min at 25° C. in a shaking water bath. The reaction is terminated by washing the tubes with 10 mL of ice-cold 50 mM Tris HCl using a Brandel cell harvesting system using Whatman GF/B filters which have been soaked at least 4 hours at room temperature in 0.01% (w:v) polyethylenimine to collect the membranes. The filters are deposited in scintillation vials and read in a Beckman LS 6000 LL Scintillation Counter. The binding constant $K_i$ is calculated by standard methods and is typically the mean of several such determinations. The $K_i$ values may be converted to negative logarithms and expressed as $-\log$ molar $K_i$ (ie. $pK_i$).

In an initial use of this assay, the $IC_{50}$ measured for the standard compound L-659,877 was found to be 30 nM versus $^3$H-NKA binding to MELM.

The selectivity of a Compound for binding at the NK2 receptor may be shown by determining its binding at other receptors using standard assays, for example, one using a tritiated derivative of SP in a tissue preparation selective for NK1 receptors or one using a tritiated derivative of NKB in a tissue preparation selective for NK3 receptors.

Guinea Pig Assay (Test B)

In the test described below either NKA or [□-Ala$^8$]-NKA (4–10) is used as an agonist. The chosen agonist is referred to as AG throughout the description. The ability of a Compound to antagonize the action of AG in a pulmonary tissue may be demonstrated using a functional assay in guinea pig trachea, which is carried out as follows.

Male guinea pigs are killed by a sharp blow to the back of the head. The trachea are removed, trimmed of excess tissue and divided into two segments. Each segment is suspended as a ring between stainless steel stirrups in water-jacketed (37.5° C.) tissue baths containing a physiological salt solution of the following composition (mM): NaCl, 119; KCl 4.6; $CaCl_2$, 1.8; $MgCl_2$, 0.5; $NaH_2PO_4$, 1; $NaHCO_3$, 25; glucose, 11; thiorphan, 0.001; and indomethacin, 0.005; gassed continuously with 95% $O_2$-% 5 $CO_2$. Initial tension placed on each tissue is 1 g, which is maintained throughout a 0.5 to 1.5 hour equilibration period before addition of other drugs. Contractile responses are measured on a Grass polygraph via Grass FT-03 force transducers.

Tissues are challenged repetitively with a single concentration of AG (10 nM) with intervening 30 min periods with washing to allow the tension to return to baseline levels. The magnitude of the contractions to AG reaches a constant level after two challenges, and each Compound is tested for inhibition of responses to AG by addition to the tissue bath 15 minutes before the third or subsequent exposure to the agonist. The contractile response to AG in the presence of Compound is compared to that obtained with the second AG challenge (in the absence of Compound). Percent inhibition is determined when a Compound produces a statistically significant (p<0.05) reduction of the contraction and is calculated using the second contractile response as 100%.

Potencies of selected Compounds are evaluated by calculating apparent dissociation constants ($K_B$) for each concentration tested using the standard equation:

$$K_B = [\text{antagonist}]/(\text{dose ratio}-1)$$

where dose ratio=antilog[(AG $-\log$ molar $EC_{50}$ without Compound)−(AG $-\log$ molar $EC_{50}$ with Compound)]. The $K_B$ values may be converted to the negative logarithms and expressed as $-\log$ molar $K_B$ (i.e. $pK_B$). For this evaluation, complete concentration-response curves for AG are obtained in the absence and presence of Compound (30 min incubation period) using paired tracheal rings. The potency of AG is determined at 50% of its own maximum response level in each curve. The $EC_{50}$ values are converted to the negative logarithms and expressed as $-\log$ molar $EC_{50}$. Maximum contractile responses to AG are determined by expressing the maximum response to AG as a percentage of the contraction caused by carbachol (30 μM), added after the initial equilibration period. When a statistically significant (p<0.05) reduction of the maximum response to AG is produced by a Compound, the percent inhibition is calculated relative to the percentage of carbachol contraction in the untreated, paired tissue used as 100%.

Clinical studies to demonstrate the efficacy of a Compound may be carried out using standard methods. For example, the ability of a Compound to prevent or treat the symptoms of asthma or asthma-like conditions may be demonstrated using a challenge of inhaled cold air or allergen and evaluation by standard pulmonary measurements such as, for example, $FEV_1$ (forced expiratory volume in one second) and FVC (forced vital capacity), analyzed by standard methods of statistical analysis.

It will be appreciated that the implications of a Compound's activity in Test A or Test B is not limited to asthma, but rather, that the test provides evidence of general antagonism of NKA. In general, the Compounds which were tested demonstrated statistically significant activity in Test A with a $K_i$ of 1 μM or much less. For example, the compound described in Example 2 was typically found to have a $K_i$ of 4.1 nM. In Test B, a $pK_B$ of 5 or greater was typically measured for a Compound. For example, a $pK_B$ of 8.7 was measured for the compound described in Example 2. It should be noted that there may not always be a direct correlation between the activities of Compounds measured as $K_i$ values in Test A and the values measured in other assays, such as the $pK_B$ measured in Test B.

As discussed above, Compounds of the invention possesses NKA antagonist properties. Accordingly, they antagonizes at least one of the actions of NKA which are known to include bronchoconstriction, increased microvascular permeability, vasodilation and activation of mast cells. Accordingly, one feature of the invention is the use of a compound of formula I; or the N-oxide of said compound of formula I at the piperidino nitrogen indicated by Δ; or a pharmaceutically acceptable salt of said compound of formula I or said N-oxide; or a quaternary ammonium salt of said compound of formula I in which the piperidino nitrogen indicated by Δ is a quadricovalent ammonium nitrogen wherein the fourth radical on the nitrogen is (1–4C)alkyl or benzyl and the associated counterion is a pharmaceutically acceptable anion; as defined above, in the treatment of a disease in a human or other mammal in need thereof in which NKA is implicated and antagonism of its action is desired, such as for example the treatment of asthma or a related disorder. In addition, another feature of the invention is provided by the use of a compound of formula I; or the N-oxide of said compound of formula I at the piperidino nitrogen indicated by Δ; or a pharmaceutically acceptable salt of said compound of formula I or said N-oxide; or a quaternary ammonium salt of said compound of formula I in which the piperidino nitrogen indicated by Δ is a quadricovalent ammonium nitrogen wherein the fourth radical on the nitrogen is (1–4C)alkyl or benzyl and the associated counterion is a pharmaceutically acceptable anion; as defined above, as a pharmacological standard for the development and standardization of new disease models or assays for use in developing new therapeutic agents for treating the diseases in which NKA is implicated or for assays for their diagnosis.

When used in the treatment of such a disease, a Compound is generally administered as an appropriate pharmaceutical composition which comprises a compound of formula I; or the N-oxide of said compound of formula I at the piperidino nitrogen indicated by Δ; or a pharmaceutically acceptable salt of said compound of formula I or said N-oxide; or a quaternary ammonium salt of said compound of formula I in which the piperidino nitrogen indicated by Δ is a quadricovalent ammonium nitrogen wherein the fourth radical on the nitrogen is (1–4C)alkyl or benzyl and the associated counterion is a pharmaceutically acceptable anion; as defined above, and a pharmaceutically acceptable diluent or carrier, the composition being adapted for the particular route of administration chosen. Such a composition is provided as a further feature of the invention. It may be obtained employing conventional procedures and excipients and binders, and it may be one of a variety of dosage forms. Such forms include, for example, tablets, capsules, solutions or suspensions for oral administration; suppositories for rectal administration; sterile solutions or suspensions for administration by intravenous or intramuscular infusion or injection; aerosols or nebulizer solutions or suspensions for administration by inhalation; or powders together with pharmaceutically acceptable solid diluents such as lactose for administration by insufflation.

For oral administration a tablet or capsule containing up to 250 mg (and typically 5 to 100 mg) of a compound of formula I may conveniently be used. For administration by inhalation, a compound of formula I will be administered to humans in a daily dose range of, for example, 5 to 100 mg, in a single dose or divided into two to four daily doses. Similarly, for intravenous or intramuscular injection or infusion a sterile solution or suspension containing up to 10% w/w (and typically 0.05 to 5% w/w) of a compound of formula I may conveniently be used.

The dose of a compound of formula I to be administered will necessarily be varied according to principles well known in the art taking account of the route of administration and the severity of the condition and the size and age of the patient under treatment. However, in general, the compound of formula I will be administered to a warm-blooded animal (such as man) so that a dose in the range of, for example, 0.01 to 25 mg/kg (and usually 0.1 to 5 mg/kg) is received. It will be understood that generally equivalent amounts of an N-oxide or a pharmaceutically acceptable salt or a quaternary ammonium salt of a compound of formula I may be used.

The invention will now be illustrated by the following non-limiting examples in which, unless stated otherwise:

(i) temperatures are given in degrees Celsius (° C.); operations were carried out at room or ambient temperature, that is, at a temperature in the range of 18–25° C.;

(ii) organic solutions were dried over anhydrous sodium sulfate; evaporation of solvent was carried out using a rotary evaporator under reduced pressure (600–4000 pascals; 4.5–30 mm Hg) with a bath temperature of up to 60° C.;

(iii) chromatography means 'flash chromatography' (method of Still) carried out on Merck Kieselgel (Art 9385 from E. Merck, Darmstadt, Germany); reversed phase silica gel means octadecylsilane (ODS) coated support having a particle diameter of 32–74μ, known as "PREP-40-ODS" (Art 731740-100 from Bodman Chemicals, Aston, Pa., USA); thin layer chomatography (TLC) was carried out on 0.25 mm silica gel GHLF plates (Art 21521 from Analtech, Newark, Del., USA);

(iv) in general, the course of reactions was followed by TLC and reaction times are given for illustration only;

(v) melting points are uncorrected and (d) indicates decomposition; the melting points given are those obtained for the materials prepared as described; polymorphism may result in isolation of materials with different melting points in some preparations;

(vi) final products had satisfactory nuclear magnetic resonance (NMR) spectra and were substantially pure by TLC;

(vii) yields are given for illustration only and are not necessarily those which may be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 300 MHz using CDCl$_3$ as solvent; conventional abbreviations for signal shape are used; for AB spectra the directly observed shifts are reported.

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume: volume (v/v) terms; and (xii) mass spectra (MS) were run with an electron energy of 70 electron volts in the chemical ionization mode using a direct exposure probe; generally, only peaks which indicate the parent mass are reported.

EXAMPLE 1

N-[2-(3,4-Dichlorophenyl)-4-[4-(2-oxo-1,3-oxazolidin-3-yl)piperidino]butyl]-N-methylbenzamide hydrochloride N-[2-(3,4-Dichlorophenyl)-4-oxobutyl]-N-methylbenzamide (0.823 g) in methanol (4 mL) was added to a solution of 4-(2-oxo-1,3-oxazolidin-3-yl)piperidine (0.600 g) and acetic acid (0.20 mL) in methanol (8 mL).

After 5 minutes, sodium cyanoborohydride (0.220 g) in methanol (4 mL) was added in a single portion. After being stirred for 3 hours, the reaction mixture was diluted with aqueous sodium bicarbonate, stirred for 30 minutes, and extracted with dichloromethane. The organic extracts were dried, evaporated, and chromatographed, with dichloromethane:methanol (gradient 98:2, 90:10) as eluent. The resulting material was dissolved in dichloromethane, precipitated as the hydrochloride salt with ethereal hydrogen chloride, evaporated, and placed under high vacuum overnight to give the title compound as a white solid (0.88 g); MS: m/z=504(M+1); Analysis for $C_{26}H_{31}Cl_2N_3O_3 \cdot 1.20$ HCl: Calculated: C, 56.96; H, 5.92; N, 7.66. Found: C, 57.02; H, 6.05; N, 7.62.

The intermediate N-[2-(3,4-dichlorophenyl)-4-oxobutyl]-N-methylbenzamide was prepared as follows.

a. 1-Bromo-2-(tetrahydropyran-2-yloxy)ethane. To a mechanically stirred solution of dihydropyran (1 L) and a strong acid ion exchange resin (10.0 g) in hexane (2 L) was added 2-bromoethanol (985 g) dropwise over a period of 1.5 hours in a cold water bath to maintain an internal temperature of 35–40° C. After being stirred overnight at room temperature, the reaction mixture was chromatographed with hexane (6 L). The eluate was evaporated to give an amber liquid which was distilled through a 2 inch vigreux column, collecting the material boiling between 75–95° C. (3,300–4,700 Pa). This material was redistilled to give the ether as an oil (1195.5 g); bp 80–90° C. (2666 Pa); NMR: 4.68 (m,1), 4.01 (m,1), 3.89 (m,1), 3.77 (m,1), 3.52 (m,3), 1.75–1.50 (m,6).

b. α-[2-(Tetrahydropyran-2-yloxy)ethyl]-3,4-dichlorophenyl-acetonitrile. To a solution of sodium hydride (218.0 g of a 55% oil suspension) in tetrahydrofuran (4 L) at 10° C. in an ice/water bath was added 3,4-dichlorophenylacetonitrile (893.0 g) in tetrahydrofuran (2 L) over a period of 45 minutes, and the resulting solution was allowed to stir for 2 hours at room temperature. The mixture was cooled in an ice/water bath, and 1-bromo-2-(tetrahydropyran-2-yloxy)ethane (1076.0 g) was dropped in as a neat oil over a period of 25 minutes. The mixture was stirred overnight at room temperature and divided into four 2-liter portions. Each portion was diluted with saturated ammonium chloride (3 L) and extracted with ether (500 mL). The combined organic layers were washed with aqueous ammonium chloride, dried, and evaporated. The resulting material was chromatographed, with hexane:dichloromethane (gradient 100:0, 0:100) as eluent, to give the nitrile as an oil (932 g); NMR: 7.47 (m,4), 7.20 (m,2), 4.57 (m,2), 4.08 (m,2), 3.85 (m,4), 3.54 (m,3), 3.37 (m,1), 2.15 (m,4), 1.77 (m,4), 1.56 (m,8).

c. 2-(3,4-Dichlorophenyl)-4-(tetrahydropyran-2-yloxy)butyl-amine. To a solution of the above nitrile (128.3 g) in 95% ethanol (1.1 L) and concentrated ammonium hydroxide (550 mL) was added Raney Nickel (25.0 g). The mixture was hydrogenated under a hydrogen atmosphere at 3.6 bars for 1.5 days. The mixture was filtered through diatomaceous earth to remove the catalyst, and the resulting filtrate was evaporated. The resulting material was chromatographed, with dichloromethane:methanol (gradient 100:0, 95:5) as eluent, to give the amine as an oil (91 g); NMR: 7.40 (s,1), 7.38 (s,1), 7.32 (d,1, J=2.1), 7.28 (d,1, J=2.0), 7.07 (dd,1, J=2.1, 4.9), 7.04 (dd,1, J=2.1, 4.9), 4.50 (m,1), 4.43 (m,1), 3.70 (m,4), 3.45 (m,2), 3.27 (m,1), 3.17 (m,1), 2.97–2.75 (m,6), 2.00 (m,2), 1.82–1.66 (m,6), 1.53 (m,8), 1.18 (broad s,4); MS: m/z=318(M+1).

d. N-[2-(3,4-Dichlorophenyl)-4-(tetrahydropyran-2- yloxy)butyl]-benzamide. To a solution of the amine (2.5 g) in dichloromethane (35 mL) was added triethylamine (1.1 mL) and benzoic anhydride (1.85 g), and the resulting solution was allowed to stir for 45 minutes. The mixture was washed with 0.2 N hydrochloric acid, 1 N sodium hydroxide, and water, dried, and evaporated to give the amide as an oil (3.3 g); NMR: 7.63 (m,4), 7.46 (m,2), 7.37 (m,8), 7.09 (m,2), 6.22 (m,2), 4.50 (m,1), 4.43 (m,1), 3.8 (m,5), 3.63 (m,1) 3.5 (m,4), 3.36 (m,1), 3.23 (m,1), 3.11 (m,2), 2.06 (m,2), 1.90–1.77 (m,4), 1.68 (m,2), 1.51 (m,8); MS: m/z=338[(M+1)-tetrahydropyranyl].

e. N-[2-(3,4-Dichlorophenyl)-4-(tetrahydropyran-2- yl-oxy)butyl]-N-methylbenzamide. To a solution of the above amide (3.3 g) in dimethylsulfoxide (20 mL) was added powdered potassium hydroxide (1.6 g), followed by iodomethane (1.0 mL) after 15 minutes. After 1 hour, the mixture was diluted with water and extracted with dichloromethane. The combined organic extracts were dried and evaporated to give the amide as an oil (3.1 g); MS: m/z=352[(M+1)-tetrahydropyranyl].

f. N-[2-(3,4-Dichlorophenyl)-4-hydroxybutyl]-N- methylbenzamide. To a solution of the above amide (10.5 g) in tetrahydrofuran (100 mL) was added 6 N hydrochloric acid (50 mL), and the resulting solution was allowed to stir overnight. The mixture was neutralized with 10 N sodium hydroxide, diluted with water, and extracted with dichloromethane. The organic layer was dried and evaporated. The resulting yellow solid was suspended in ether and filtered to give the alcohol as a white solid (8.4 g); MS: m/z=352(M+1).

g. N-[2-(3,4-Dichlorophenyl)-4-oxobutyl]-N- methylbenzamide. To a solution of oxalyl chloride (2.6 mL) in dichloromethane (60 mL) at −78° C. was added dimethylsulfoxide (4.2 mL) in dichloromethane (30 mL), followed by the above alcohol (8.3 g) in dimethylsulfoxide (6 mL) and dichloromethane (30 mL). The resulting solution was allowed to stir for 30 minutes, and triethylamine (16.4 mL) was added. The mixture was allowed to warm to room temperature, diluted with dichloromethane, washed with 1 N hydrochloric acid, saturated aqueous sodium bicarbonate, and water, dried, and evaporated. The resulting yellow solid was suspended in ether and filtered to give the the aldehyde as a white solid (6.4 g); MS: m/z=350(M+1).

The intermediate 4-(2-oxo-1,3-oxazolidin-3-yl)piperidine was prepared as follows.

h. 1-Benzyloxycarbonyl-4-(2-hydroxyethylamino)piperidine. 1-Benzyloxycarbonyl-4-oxopiperidine (2.5 g) in methanol (7.0 mL) was added to a solution of ethanolamine (1.3 mL) and acetic acid (1.2 mL) in methanol (20 mL). After 5 minutes, sodium cyanoborohydride (1.35 g) in methanol (6 mL) was added in a single portion. After being stirred overnight, the reaction mixture was diluted with aqueous sodium bicarbonate, stirred for 30 minutes, and extracted with dichloromethane. The combined organic extracts were evaporated, dissolved in 1 N hydrochloric acid, and washed with dichloromethane. The aqueous phase was basified with 1 N sodium hydroxide and extracted with dichloromethane. The extracts were dried and evaporated to give the amino alcohol as an oil (1.7 g); NMR (CD$_3$OD): 7.34 (m,5), 5.10 (s,2), 4.13 (m,2), 3.64 (m,2), 2.86 (m,2), 2.73 (m,2), 2.67 (m,1), 1.90 (m,2), 1.25 (m,2); MS: m/z=279(M+1).

i. 1-Benzyloxycarbonyl-4-(2-oxo-1,3-oxazolidin-3-yl)piperidine. A solution of the amino alcohol (1.7 g) and 1,1'-carbonyldiimidazole (2.4 g) in chloroform (30 mL)

was heated at reflux for 6 hours. The reaction mixture was diluted with dichloromethane and washed with 1 N sodium hydroxide and water. The separated organic phase was dried and evaporated to give the oxazolidin-3-yl piperidine as a viscous oil (1.9 g); NMR: 7.35 (m,5), 5.13 (s,2), 4.34 (m,4), 3.89 (m,1), 3.49 (m,2), 2.86 (m,2), 1.78 (m,2), 1.58 (m,2); MS: m/z=305(M+1).

j. 4-(2-Oxo-1,3-oxazolidin-3-yl)piperidine. A solution of the above oxazolidin-3-ylpiperidine (1.85 g) and 20% palladium hydroxide on carbon (0.340 g) in ethanol (30 mL) was stirred overnight under 1 bar of hydrogen. The reaction mixture was filtered through diatomaceous earth and the filtrate was evaporated to give the title compound (0.950 g) as a white solid; NMR (CD$_3$OD): 4.35 (m,2), 3.75 (m,1), 3.62 (m,2), 3.20 (m,2), 2.76 (m,2), 1.75 (m,4); MS: m/z=171(M+1).

EXAMPLE 2

(S)-N-[2-(3,4-Dichlorophenyl)-4-(2-oxoperhydro-1,3-oxazin-3-yl)piperidino]butyl]-N-methylbenzamide hydrochloride Using the procedure of Example 1, replacing 4-[4-(2-oxo-1,3-oxa-zolidin-3-yl)piperidine with 4-(2-oxoperhydro-1,3-oxazin-3-yl)-piperidine, and N-[-2-(3,4-dichlorophenyl)-4-oxobutyl]-N-methyl-benzamide by the (S)-enantiomer, the title compound was obtained as a white solid; MS: m/z=518 (M+1); Analysis for C$_{27}$H$_{33}$Cl$_2$N$_3$O$_3$.1.55 HCl.0.20 (C$_2$H$_5$)$_2$O: Calculated: C, 56.61; H, 6.24; N, 7.12. Found: C, 56.54; H, 6.60; N, 7.38.

The (S)-N-[2-(3,4-dichlorophenyl)-4-oxobutyl]-N-methyl-benzamide was prepared as follows.

a. 2-(3,4-Dichlorophenyl)-4-hydroxybutylamine. To a mechanically stirred solution of 2-(3,4-dichlorophenyl)-4-(tetrahydropyran-2-yloxy)butylamine (550 g) in methanol (3300 mL) was added in one portion 6.0 N hydrochloric acid (352 mL), resulting in a slight exotherm. After being stirred for 3 hours, the reaction mixture was evaporated, and the residue was diluted with water to 3 L volume. This solution was extracted with ether (2 times 500 mL), basified with sodium hydroxide pellets (100 g), and extracted with ethyl acetate (4 times 500 mL). The combined ethyl acetate extracts were washed (800 mL saturated sodium chloride), dried, and evaporated to give the alcohol as an amber oil (367 g) that solidified under high vacuum; NMR: 7.39 (d,1, J=8.2), 7.28 (d,1, J=2.0), 7.04 (dd,1, J=8.2, 2.0), 3.65 (m,1), 3.50 (m,1), 2.90 (m,2), 2.71 (m,1), 2.25 (m,2), 1.86 (m,2).

b. (S)-2-(3,4-Dichlorophenyl)-4-hydroxybutylamine. To a mechanically stirred solution of D-tartaric acid (222 g) in methanol (4 L) at reflux was added the above amino alcohol (342 g) in warm methanol (2 L) in one portion and washed down with additional methanol (1 L). The mixture was heated to reflux. Crystals began to form before attaining the boiling point. After 1.5 hours at reflux, the solution was gradually cooled to room temperature and stirred for 3 days. The first crop of tartrate salt was collected by suction filtration and dried in a vacuum oven at 60° C. to give the product (232 g). This material was taken up in methanol (13.5 L) at boiling, and held at reflux for 1 hour allowing 1 L of methanol to distil off. The mixture was allowed to cool gradually to room temperature and stirred for 4 days. The first crop of crystals was collected by suction filtration and dried to give a solid (178.8 g). The methanol filtrate was evaporated to approximately 3 L volume. The resulting suspension was heated back to reflux to give a clear solution that was allowed to cool gradually to room temperature with stirring. A second crop of crystals (43.8 g) was collected. The combined crops of resolved amino alcohol tartrates (222.6 g) were taken up in 1.0 N sodium hydroxide (1.5 L) and extracted with dichloromethane (4 times 500 mL). The combined organic extracts were washed with brine, dried, and evaporated to give the optically enriched amino alcohol as an off-white solid (135.4 g); mp 80–2° C.; NMR (CD$_3$OD): 7.47 (d,1, J=8.3), 7.42 (d,1, J=2.1), 7.17 (dd,1, J=8.2, 2.1), 3.47 (m,1), 3.34 (m,1), 2.83 (m,3), 1.92 (m,1), 1.74 (m,1); MS: m/z=324(M+1).

c. Ethyl (S)-N-[2-(3,4-dichlorophenyl)- 4-hydroxybutyl]-carbamate. Ethyl chloroformate (25.5 g) was added dropwise over 20 minutes to a mechanically stirred solution of the above amino alcohol (50.0 g) and triethylamine (24.9 g) in dichloromethane (600 mL) cooled to −30° C. The internal temperature was maintained at −20 to −25° C. during the addition. The reaction mixture was then allowed to warm gradually to room temperature over a 4 hour period, and washed (1 N hydrochloric acid, saturated aqueous sodium bicarbonate, and saturated aqueous sodium chloride). The separated dichloromethane phase was dried and evaporated to give the carbamate as a yellow oil (65.3 g); NMR (CD$_3$OD): 7.44 (d,1, J=8.3), 7.38 (d,1, J=2.1), 7.15 (dd,1, J=8.3, 2.1), 3.99 (q,2, J=7.1), 3.45 (m,1), 3.29 (m,3), 2.97 (m,1), 1.92 (m,1), 1.75 (m,1), 1.16 (t,3, J=7.1); MS: m/z=306(M+1).

d. (S)-N-Methyl-2-(3,4-dichlorophenyl)-4- hydroxybutylamine. The above carbamate (65.3 g) in tetrahydrofuran (500 mL) was added dropwise over 30 minutes to a mechanically stirred suspension of lithium aluminum hydride (16.0 g) in tetrahydrofuran (200 mL). The internal temperature rose to 45° C. during the addition. The reaction mixture was heated at reflux for 1 hour, then cooled to room temperature and stirred overnight. The mixture was cooled in an ice bath, and saturated aqueous sodium sulfate (50 mL) was added dropwise over 45 minutes. After an additional hour of stirring, solid anhydrous sodium sulfate (50 g) was added. After being stirred for 30 minutes, the mixture was filtered through diatomaceous earth, and the filtrate was evaporated to give the methylamine as a yellow oil (52.9 g); NMR: 7.37 (d,1, J=8.2), 7.27 (d,1, J=2.0), 7.01 (dd,1, J=8.2, 2.1), 3.69 (m,1), 3.53 (m, 1), 3.40 (m,2), 2.76 (m,3), 2.45 (m,3), 1.89 (m,2); MS: m/z=248(M+1).

e. (S)-N-[2-(3,4-Dichlorophenyl)-4-hydroxybutyl]-N- methylbenz-amide. Benzoyl chloride (31.5 g) in dichloromethane (200 mL) was added dropwise over 45 minutes to a mechanically stirred solution of the above amine (52.9 g) and triethylamine (54.0 g) in dichloromethane (1 L) cooled in an ice bath to maintain an internal temperature of 5–8° C. The reaction mixture was allowed to stir for 3 hours at room temperature, and then washed (1 N hydrochloric acid, brine). The separated dichloromethane layer was evaporated to give a yellow oil which was chromatographed, with dichloromethane:methanol (gradient 100:0, 95:5) as eluent, to give the benzamide as a white solid (65.6 g); mp 123–5° C.; MS: m/z=352(M+1); [a]$_D$=−18.3° (c=2.46, CH$_3$OH).

f. (S)-N-[2-(3,4-Dichlorophenyl)-4-oxobutyl]-N- methylbenzamide. The above alcohol (12.9 g) in dichloromethane (150 mL) was cannulated into a solution of Dess-Martin periodinane (18.6 g) and tert-butanol (4.5 mL) in dichloromethane (150 mL). After being stirred for 5 minutes, the reaction mixture was diluted with ether (600 mL) and a solution of sodium bicarbonate (19.7 g) and sodium thiosulfate pentahydrate (64.5 g) in water (825 mL). The biphasic system was vigorously stirred until both layers became clear (approximately 30 minutes). The separated organic layer was washed (saturated aqueous sodium bicarbonate), dried, and evaporated. The crude material was chromatographed, with dichloromethane:ether (1:1) as eluent, to give the aldehyde as a white solid (9.7 g) by precipitation and filtration from ether; MS: m/z=350(M+1).

The intermediate 4-(2-oxoperhydro-1,3-oxazin-3-yl)piperidine was prepared as follows.

g. 1-Benzyloxycarbonyl-4-(3-hydroxypropylamino)piperidine. Using the procedure of Example 1.h, replacing ethanolamine with 3-amino-1-propanol, the amino piperidine was obtained as an oil; NMR (CD$_3$OD): 7.35 (m,5), 5.10 (s,2), 4.12 (m,2), 3.62 (t,2, J=6.2), 2.86 (m,2), 2.71 (m,2), 2.65 (m,1), 1.90 (m,2), 1.71 (m,2), 1.24 (m,2); MS: m/z=293(M+1).

h. 1-Benzyloxycarbonyl-4-(2-oxoperhydro-1,3-oxazin-3-yl)-piperidine. Using the procedure of Example 1.i, replacing 1-benzyloxycarbonyl-4-(2-hydroxyethylamino)piperidine with 1-benzyloxycarbonyl-4-(3-hydroxypropylamino)piperidine, the oxazin-3-yl piperidine was obtained as an oil; NMR (CD$_3$OD): 7.35 (m,5), 5.11 (s,2), 4.22 (m,5), 3.24 (m,2), 2.88 (m,2), 1.99 (m,2), 1.69 (m,4); MS: m/z=319(M+1).

i. 4-(2-Oxoperhydro-1,3-oxazin-3-yl)piperidine. Using the procedure of Example 1.j, replacing 1-benzyloxycarbonyl-4-(2-oxo-1,3-oxazolidin-3-yl)piperidine with 1-benzyloxycarbonyl-4-(2-oxoperhydro-1,3-oxazin-3-yl)piperidine, the deprotected piperidine was obtained as an amorphous, white solid; NMR (CD$_3$OD): 4.24 (m,2), 4.12 (m,1), 3.32 (m,2), 3.22 (m,2), 2.78 (m,2), 2.03 (m,2), 1.79 (m,4); MS: m/z=185(M+1).

EXAMPLE 3

(S)-N-[2-(3,4-Dichlorophenyl)-4-[4-(2-oxoimidazolidin-1-yl)piperidino]butyl]-N-methylbenzamide hydrochloride A stirred solution of (S)-N-[4-[4- (2-aminoethylamino)piperidino]-2-(3,4-dichlorophenyl)butyl]-N-methylbenzamide (0.356 g) and 1,1'-carbonyldiimidazole (0.157 g) in chloroform (6 mL) was heated at reflux for 2 hours. The reaction mixture was diluted with dichloromethane, washed (aqueous sodium bicarbonate), dried, evaporated, and chromatographed, with dichloromethane:methanol (gradient 98:2, 90:10) as eluent. The resulting material was dissolved in dichloromethane, precipitated as the hydrochloride salt with ethereal hydrogen chloride, evaporated, and placed under high vacuum overnight to give the title compound as a white solid (0.244 g); MS: m/z=503 (M+1); Analysis for C$_{26}$H$_{32}$Cl$_2$N$_4$O$_2$.1.70 HCl.0.20 (C$_2$H$_5$)$_2$O: Calculated: C, 55.47; H, 6.20; N, 9.65. Found: C, 55.47; H, 6.35; N, 9.44.

The intermediate (S)-N-[4-[4- (2-aminoethylamino)piperidino]-2-(3,4-dichlorophenyl)butyl]-N-methylbenzamide was prepared as follows.

a. 1-Benzyloxycarbonyl-4-(2-aminoethylamino)piperidine. 1-Benzyloxycarbonyl-4-oxopiperidine (12.0 g) in methanol (72 mL) was added to a stirred solution of ethylenediamine (5.2 mL) and acetic acid (8.8 mL) in methanol (72 mL). After 15 minutes, sodium cyanoborohydride (9.7 g) in methanol (72 mL) was added in a single portion. After being stirred overnight, the reaction mixture was evaporated; and the residue was dissolved in 1 N hydrochloric acid (100 mL). Concentrated hydrochloric acid was added dropwise and stirring was continued until the evolution of gas ceased. The acidic aqueous mixture was washed with dichloromethane, basified to pH 10 with 10 N sodium hydroxide, and extracted with dichloromethane. The dichloromethane extracts were dried and evaporated to give the diamine as a viscous oil (7.5 g); NMR (CD$_3$OD): 7.35 (m,5), 5.10 (s,2), 4.12 (m,2), 2.89 (m,2), 2.70 (m,5), 1.90 (m,2), 1.24 (m,2); MS: m/z=278 (M+1).

b. 1-Benzyloxycarbonyl-4-[(2,2,2-trifluoroacetyl)[2-(2,2,2-trifluoroacetylamino)-ethyl]amino]piperidine. Trifluoroacetic anhydride (10.5 mL) was added to a solution of the above diamine (7.5 g) in chloroform (90 mL). After being stirred overnight, the reaction mixture was cooled to 0° C.; and triethylamine (8.3 mL) was dropped in. After 1 hour, the mixture was diluted with dichloromethane, washed (1 N hydrochloric acid, aqueous sodium bicarbonate), dried, evaporated, and chromatographed, with dichloromethane:methanol (98:2) as eluent, to give the trifluoroacetylated piperidine as a white foam (8.9 g); NMR (CD$_3$OD): 7.35 (m,5), 5.12 (s,2), 4.28 (m,2), 3.95 (m,1), 3.48 (m,4), 2.90 (m,2), 1.78 (m,4); MS: m/z=470 (M+1).

c. 4-[(2,2,2-Trifluoroacetyl)[2-(2,2,2-trifluoroacetylamino)-ethyl]amino]piperidine. Using the procedure of Example 1.j, replacing 1-benzyloxycarbonyl-4-(2-oxo-1,3-oxazolidin-3-yl)piperidine with 1-benzyloxycarbonyl-4-[(2,2,2-trifluoroacetyl)[2-(2,2,2-trifluoroacetylamino)ethyl]amino]piperidine, the 1-deprotected piperidine was obtained as a yellow oil; NMR (CD$_3$OD): 3.84 (m,1), 3.51 (m,4), 3.12 (m,2), 2.61 (m,2), 1.74 (m,4); MS: m/z=336 (M+1).

d. (S)-N-[2-(3,4-Dichlorophenyl)-4-[4- [(2,2,2-trifluoroacetyl)[2-(2,2,2-trifluoroacetylamino)ethyl]amino]piperidino]-butyl]-N-methylbenzamide. Using the procedure of Example 1, replacing 4-(2-oxo-1,3-oxazolidin-3-yl)piperidine with 4-[(2,2,2-trifluoro-acetyl)[2-(2,2,2-trifluoroacetylamino)ethyl]amino]piperidine, and N-[-2-(3,4-dichlorophenyl)-4-oxobutyl]-N-methylbenzamide with the (S)-enantiomer, the N-methylbenzamide was obtained as a viscous oil; MS: m/z=669(M+1).

e. (S)-N-[4-[4-(2-Aminoethylamino)piperidino]- 2-(3,4-dichloro-phenyl)butyl]-N-methylbenzamide. A solution of the crude product from Example 3.d. (2.5 g) in 20% aqueous potassium hydroxide (8.5 mL) and methanol (11 mL) was stirred for 1 hour. The reaction mixture was acidified to pH 2 with 1 N hydrochloric acid and washed 3 times with dichloromethane. The aqueous phase was then basified to pH 10 with 10 N sodium hydroxide and extracted with dichloromethane. The extracts were dried and evaporated to give the diamine as a viscous oil (1.8 g); MS: m/z=477(M+1).

EXAMPLE 4

(S)-N-[2-(3,4-Dichlorophenyl)-4-[4-(2-thioxoimidazolidin-1-yl)piperidino]butyl]-N-methylbenzamide hydrochloride Using the procedure of Example 3, replacing 1,1'-carbonyl-diimidazole with 1,1'-thiocarbonyldi-2(1H)-pyridone and stirring at room temperature for 1.5 hours instead of reflux, the title compound was obtained as a white solid; MS: m/z=519(M+1); Analysis for $C_{26}H_{32}Cl_2N_4OS \cdot 1.70$ $HCl \cdot 0.10$ $(C_2H_5)_2O$: Calculated: C, 53.84; H, 5.93; N, 9.51. Found: C, 53.89; H, 5.89; N, 9.48.

EXAMPLE 5

(S)-N-[2-(3,4-Dichlorophenyl)-4-[4-(2-oxoperhydropyrimidin-1-yl)piperidino]butyl]-N-methylbenzamide dihydrochloride Using the procedure of Example 3, replacing (S)-N-[4-[4-(2-aminoethylamino)-piperidino]-2-(3,4- dichlorophenyl)-butyl]-N-methylbenzamide with (S)-N-[-4-[4-(3-aminopropylamino)piper-idino]-2-(3,4- dichlorophenyl)butyl]-N-methylbenzamide, the title compound was obtained as a white solid; MS: m/z=517(M+1); Analysis for $C_{27}H_{34}Cl_2N_4O_2 \cdot 2.60$ $HCl \cdot 0.13$ $(C_2H_5)_2O$: Calculated: C, 53.14; H, 6.14; N, 9.00. Found: C, 53.14; H, 6.31; N, 9.16.

The intermediate (S)-N-[4-[4- (3-aminopropylamino)piperidino]-2-(3,4-dichlorophenyl)butyl]-N-methylbenzamide was prepared as follows.

a. 1-Benzyloxycarbonyl-4-(3-aminopropylamino)piperidine. Using the procedure of Example 3.a, replacing ethylenediamine with 1,3-diaminopropane, the piperidine was obtained as a viscous oil; MS: m/z=292(M+1); NMR ($CD_3OD$): 7.34 (m,5), 5.10 (s,2), 4.13 (m,2), 2.86 (m,2), 2.65 (m,5), 1.90 (m,2), 1.65 (m,2), 1.23 (m,2).

b. 1-Benzyloxycarbonyl-4-[2,2,2-trifluoroacetyl)-[3-(2,2,2-trifluoroacetylamino)-propyl]amino]piperidine. Using the procedure of Example 3.b, replacing 1-benzyloxycarbonyl-4-(2-amino-ethylamino)piperidine with 1-benzyloxycarbonyl-4-(3-aminopropyl-amino)piperidine and adding triethylamine to the solution before the addition of trifluoroacetic anhydride at 0° C., the trifluoroacetylated piperidine was obtained as a viscous oil; NMR: 7.36 (m,5), 5.14 (s,2), 4.35 (m,2), 3.93 (m,1), 3.35 (m,4), 2.83 (m,2), 1.87–1.74 (m,6); MS: m/z=484(M+1).

c. 4-[(2,2,2-Trifluoroacetyl)[3-(2,2,2-trifluoroacetylamino)propyl]amino]piperidine. Using the procedure of Example 1.j, replacing 1-benzyloxycarbonyl-4-(2-oxo-1,3-oxazolidin-3-yl)piperidine with 1-benzyloxycarbonyl-4-[(2,2,2-trifluoroacetyl)-[3-(2,2,2-trifluoroacetylamino)propyl]amino]piperidine, the 1-deprotected piperidine was obtained as a viscous oil; NMR ($CD_3OD$): 4.39 (m,1), 3.98 (m,1), 3.30 (m,3), 2.95 (m,1), 2.82 (m,1), 2.65 (m,2), 2.01 (m,2), 1.75 (m,2), 1.32 (m,2); MS: m/z=350 (M+1).

d. (S)-N-[2-(3,4-Dichlorophenyl)-4-[4-[(2,2,2- trifluoroacetyl)-[2-(2,2,2-trifluoroacetylamino)ethyl]amino]piperidino]butyl]-N-methylbenzamide. Using the procedure of Example 1, replacing 4-(2-oxo-1,3-oxazolidin-3-yl)piperidine by 4-[(2,2,2-trifluoroacetyl)-[3-(2,2,2-trifluoroacetylamino)propyl]amino]piperidine, and N-[2-(3,4-dichlorophenyl)-4-oxobutyl]-N-methylbenzamide by the (S)-enantiomer, the N-methylbenzamide was obtained; MS: m/z=683(M+1).

e. (S)-N-[4-[4-(3-Aminopropylamino)piperidino]- 2-(3,4-dichlorophenyl)butyl]-N-methylbenzamide. Using the procedure of Example 3.e, replacing (S)-N-[2-(3,4-dichlorophenyl)-4-[4-[(2,2,2-trifluoroacetyl) [2-(2,2,2-trifluoroacetylamino)ethyl]amino]piperidino]-butyl]-N-methylbenzamide by N-[2-(3,4- dichlorophenyl)-4-[4-[(2,2,2-trifluoroacetyl)[3-(2,2,2-trifluoroacetylamino)propyl]amino]-piperidino]butyl]-N-methylbenzamide, the diamine was obtained as a viscous oil; MS: m/z=491(M+1).

EXAMPLE 6

(S)-N-[2-(3,4-Dichlorophenyl)-4-[4-(2-thioxoperhydropyrimidin-1-yl)piperidino]butyl]-N-methylbenzamide dihydrochloride Using the procedure of Example 3, replacing 1,1'-carbonyl-diimidazole by 1,1'-thiocarbonyldiimidazole, replacing (S)-N-[4-[4-(2-aminoethylamino)piperidino]- 2-(3,4-dichloro-phenyl)butyl]-N-methylbenzamide by (S)-N-[4-[4-(3-aminopropylamino)-piperidino]-2-(3,4- dichlorophenyl)butyl]-N-methylbenzamide, and stirring overnight at room temperature instead of reflux, the title compound was obtained as a white solid; MS: m/z =533(M+1); Analysis for $C_{27}H_{34}Cl_2N_4OS \cdot 2.30$ $HCl \cdot 0.10$ $(C_2H_5)_2O$: Calculated: C, 52.67; H, 6.01; N, 8.96. Found: C, 52.57; H, 6.11; N, 8.84.

EXAMPLE 7

(S)-N-[2-(3,4-Dichlorophenyl)-4-[4-(3-methyl-2-thioxoperhydropyrimidin-1-yl) piperidino]butyl]-N-methylbenzamide hydrochloride Using the procedure of Example 1, replacing 4-(2-oxo-1,3-oxazolidin-3-yl)piperidine with 4-(3-methyl-2-thioxoperhydropyrimidin-1-yl)-piperidine, and N-[2-(3,4-dichlorophenyl)-4-oxobutyl]-N-methylbenzamide with the (S)-enantiomer, the title compound was obtained as a white solid; MS: m/z=547(M+1); Analysis for $C_{28}H_{36}Cl_2N_4OS \cdot 1.70$ $HCl \cdot 0.10$ $(C_2H_5)_2O$: Calculated: C, 55.28; H, 6.32; N, 9.08. Found: C, 55.21; H, 6.37; N, 8.88.

The intermediate 4-(3-methyl-2-thioxoperhydropyrimidin-1-yl)piperidine was prepared as follows.

a. 1-Benzyloxycarbonyl-4-(3-methylaminopropylamino)piperidine. Using the procedure of Example 3.a, replacing ethylenediamine with N-methyl-1,3-propanediamine, the title compound was obtained as a viscous oil; MS: m/z=306(M+1); NMR ($CD_3OD$): 7.34 (m,5), 5.10 (s,2), 4.13 (m,2), 2.86 (m,2), 2.70 (m,5), 2.47 (s,3), 1.91 (m,2), 1.73 (m,2),1.24 (m,2).

b. 1-Benzyloxycarbonyl-4-(3-methyl-2-thioxoperhydropyrimidin-1-yl)piperidine. A solution of the diamine (3.0 g) and 1,1'-thiocarbonyldiimidazole (1.9 g) in chloroform (70 mL) was refluxed for 1.5 hours and stirred overnight at ambient temperature. The reaction mixture was diluted with dichloromethane and washed sequentially with water, 1 N hydrochloric acid, and aqueous sodium bicarbonate. The separated organic phase was dried, evaporated, and chromatographed, with dichloromethane:ether (80:20) as eluent, to give the thiourea as a white solid (1.4 g); MS: m/z=348(M+1); NMR ($CD_3OD$): 7.35 (m,5), 5.66 (m,1), 5.11 (s,2), 4.24 (m,2), 3.35 (m,5), 3.22 (m,2), 2.88 (m,2), 1.92 (m,2), 1.72–1.55 (m,4).

c. 4-(3-Methyl-2-thioxoperhydropyrimidin-1-yl)piperidine. Trifluoromethanesulfonic acid (2.0 mL) was added to a solution of the above piperidine (1.4 g) and anisole (1.4 mL) in dichloromethane (20 mL) at 0° C. After being stirred for 2 hours, the reaction mixture was evaporated, dissolved in methanol, passed through a column of a weak base ion exchange resin, evaporated, and chromatographed, with dichloromethane:methanol (gradient 98:2, 90:10) as eluent. The resulting material was dissolved in dilute aqueous hydrochloric acid, extracted with dichloromethane (discarded), and basified with sodium hydroxide. The aqueous phase was then extracted with dichloromethane and evaporated to give the piperidine as a white solid (0.75 g); MS: m/z=214(M+1); NMR (CD$_3$OD): 5.53 (m,1), 3.36 (m,5), 3.29 (m,2), 3.08 (m,2), 2.64 (m,2), 1.94 (m,2), 1.72–1.53 (m,4).

EXAMPLE 8

(S)-N-[2-(3,4-Dichlorophenyl)-
4-[4-(2-oxo-1,3-perhydrodiazepin-1-yl)piperidino]
butyl]-N-methylbenzamide dihydrochloride Using the procedure of Example 1, replacing 4-(2-oxo-1,3-oxazolidin-3-yl)piperidine with 4-(2-oxo-1,3-perhydrodiazepin-1-yl)-piperidine, and N-[2-(3,4-dichlorophenyl)-4-oxobutyl]-N-methylbenzamide with (S)-N-[2-(3,4-dichlorophenyl)-4-oxobutyl]-N-methylbenzamide, the title compound was obtained as a white solid; MS: m/z=531(M+1); Analysis for $C_{28}H_{36}Cl_2N_4O_2$.2.10 HCl.0.20($C_2H_5$)$_2$O: Calculated: C, 55.53; H, 6.48; N, 8.99. Found: C, 55.70, H, 6.53; N, 8.91.

The intermediate 4-(2-oxo-1,3-perhydrodiazepin-1-yl)-piperidine was prepared as follows.

a. 1-Benzyloxycarbonyl-4-(4-aminobutylamino)piperidine. Using the procedure of Example 3.a, replacing ethylenediamine with 1,4-diaminobutane, the title compound was obtained as a viscous oil; MS: m/z=306(M+1); NMR (CD$_3$OD): 7.34 (m,5), 5.10 (s,2), 4.13 (m,2), 2.86 (m,2), 2.63 (m,5), 1.90 (m,2), 1.51 (m,4), 1.23 (m,2).

b. 1-Benzyloxycarbonyl-4-(2-oxo-1,3-perhydrodiazepin-1-yl )piperidine. A solution of the diamine (1.6 g) and 1,1'-carbonyldiimidazole (0.94 g) in chloroform (40 mL) was refluxed for 1 hour. The reaction mixture was diluted with dichloromethane and washed with water. The separated organic phase was dried, evaporated, and chromatographed, with dichloromethane:methanol (gradient 98:2, 90:10) as eluent, to give the urea as a white solid (0.36 g); MS: m/z=332(M+1); NMR (CD$_3$OD): 7.34 (m,5), 5.09 (s,2), 4.21 (m,3), 3.25 (m,2), 3.13 (m,2), 2.85 (m,2), 1.58 (m,6), 1.44 (m,2).

c. 4-(2-Oxo-1,3-perhydrodiazepin-1-yl)piperidine. Using the procedure of Example 1.j, replacing 1-benzyloxycarbonyl-4-(2-oxo-1,3-oxazolidin-3-yl)piperidine with 1-benzyloxycarbonyl-4-(2-oxo-1,3-perhydrodiazepin-1-yl )piperidine, the piperidine was obtained as a white solid; MS: m/z=198(M+1); NMR (CD$_3$OD): 4.16 (m,1), 3.29 (m,2), 3.21 (m,2), 3.11 (m,2), 2.65 (m,2), 1.62 (m,6), 1.48 (m,2).

EXAMPLE 9

(S)-N-[2-(3,4-Dichlorophenyl)-
4-[4-(2-oxo-5,5-dimethylperhydropyrimidin-1-yl)
piperidino]butyl]-N-methylbenzamide (S)-N-[2-(3,4-dichlorophenyl)-4-oxopropyl]-N-methylbenzamide (0.622 g) in methanol (8.0 mL) was added to a solution of 4-(2-oxo-5,5-dimethylperhydropyrimidin-1-yl)piperidine (0.400 g) and acetic acid (0.11 mL) in methanol (8.0 mL). After 5 minutes, sodium cyanoborohydride (0.119 g) in methanol (8.0 mL) was added in a single portion. After being stirred overnight, the reaction mixture was diluted with aqueous sodium bicarbonate, stirred for 30 minutes, and extracted with dichloromethane. The separated organic layer was dried, evaporated, and chromatographed, with dichloromethane:methanol (95:5) as eluent. The resulting oil, which began to crystallize upon standing, was suspended in ether and filtered to give the title compound as a white solid (0.720 g); MS: m/z=545(M+1); Analysis for $C_{29}H_{38}Cl_2N_4O_2$: Calculated: C, 63.84; H, 7.02; N, 10.26. Found: C, 63.95; H, 6.95; N, 10.15.

The intermediate 4-(2-oxo-5,5-dimethylperhydropyrimidin-1-yl)piperidine was prepared as follows.

a. 1-Benzyloxycarbonyl-4-(3-amino-2,2-dimethylpropylamino)-piperidine. Using the procedure of Example 3.a, replacing ethylenediamine with 2,2-dimethyl-1,3-propanediamine, the title compound was obtained as a viscous oil; NMR (CD$_3$OD): 7.34 (m,5), 5.10 (s,2), 4.08 (m,2), 2.93 (m,2), 2.57 (m,1), 2.46 (s,2), 2.44 (s,2), 1.89 (m,2), 1.27 (m,2), 0.89 (s,6).

b. 1-Benzyloxycarbonyl-4-(2-oxo-5,5-dimethylperhydropyrimidin-1-yl)piperidine. A solution of the diamine (3.02 g) and 1,1'-carbonyldiimidazole (2.19 g) in chloroform (40 mL) was refluxed for 3 hours. The reaction mixture was diluted with dichloromethane and washed sequentially with 1 N hydrochloric acid and aqueous sodium bicarbonate. The separated organic phase was dried, evaporated, triturated from ether, and filtered to give the urea as a white solid (1.72 g); MS: m/z=346(M+1); NMR (CD$_3$OD): 7.34 (m,5), 5.10 (s,2), 4.35 (m,1), 4.23 (m,2), 2.87 (m,6), 1.58 (m,4), 1.00 (s,6).

c. 4-(2-Oxo-5,5-dimethylperhydropyrimidin-1-yl)piperidine. Using the procedure of Example 1.j, replacing 1-benzyloxycarbonyl-4-(2-oxo-1,3-oxazolidin-3-yl)piperidine with 1-benzyloxycarbonyl-4-(2-oxo-5,5-dimethylperhydropyrimidin-1-yl)piperidine, the piperidine was obtained as a white solid; MS: m/z=212(M+1); NMR (CD$_3$OD): 4.28 (m,1), 3.10 (m,2), 2.92 (m,2), 2.89 (m,2), 2.66 (m,2), 1.59 (m,4), 1.03 (s,6).

EXAMPLE 10

(S)-N-[2-(3,4-Dichlorophenyl)-
4-[4-(3-methyl-2-oxoperhydropyrimidin-1-yl)piperidino]butyl]N-methylbenzamide citrate (S)-N-[2-(3,4-Dichlorophenyl)-4-oxobutyl]-N-methylbenzamide (0.883 g) in methanol (10.0 mL) was added to a solution of 4-(3-methyl-2-oxoperhydropyrimidin-1-yl)piperidine (0.498 g) and acetic acid (0.145 mL) in methanol (10.0 mL). After 5 minutes, sodium cyanoborohydride (0.159 g) in methanol (10.0 mL) was added in a single portion. After being stirred for 3.5 hours, the reaction mixture was diluted with aqueous sodium bicarbonate, stirred for 30 minutes, and extracted with dichloromethane. The separated organic layer was dried, evaporated, and chromatographed, with dichloromethane:methanol (95:5) as eluent. The resulting oil (0.970 g) and citric acid (0.352 g) were dissolved in methanol and evaporated to give the title compound as a glass which was scraped out as a white solid (1.27 g); MS: m/z=531(M+1); Analysis for $C_{28}H_{36}Cl_2N_4O_2$.1.10$C_6H_8O_7$.0.30 H2O: Calculated: C, 55.53; H, 6.11; N, 7.48. Found: C, 55.55; H, 6.04; N, 7.46.

The intermediate 4-(3-methyl-2-oxoperhydropyrimidin-1-yl)-piperidine was prepared as follows.

a. 1-Benzyloxycarbonyl-4-(2-oxoperhydropyrimidin-1-yl)-piperidine. A stirred solution of 1-benzyloxycarbonyl-4-(3-aminopropylamino)piperidine (10.1 g) and 1,1'-carbonyldiimidazole (6.2 g) in chloroform (250 mL) was heated at reflux for 2 hours. The mixture was washed with water, and the separated organic phase was dried, evaporated, and chromatographed, with dichloromethane/methanol (90:10) as eluent, to give the urea as a white solid (7.4 g); MS: m/z=318(M+1); NMR (CDCl$_3$): 7.35

(m,5), 5.12 (s,2), 4.75 (m,1), 4.50 (m,1), 4.26 (m,2), 3.27 (m,2), 3.13 (m,2), 1.89 (m,2), 1.63 (m,4).

b. 1-Benzyloxycarbonyl-4-(3-methyl-2-oxoperhydropyrimidin-1-yl)-piperidine. Potassium tert-butoxide (19.3 mL, 1 M in tetrahydrofuran) was added to a solution of 1-benzyloxycarbonyl-4-(2-oxoperhydropyrimidin-1-yl)piperidine (3.06 g) in tetrahydrofuran (88 mL). Iodomethane (2.4 mL) was then added, and the reaction mixture was stirred for 30 minutes. The reaction mixture was diluted with dichloromethane, washed with water, and chromatographed, with dichloromethane:methanol (gradient 98:2, 90:10) as eluent. The product was triturated from ether and filtered to give the N-methyl compound as a white solid (2.78 g); MS: m/z=332(M+1); NMR (CDCl$_3$): 7.34 (m,5), 5.12 (s,2), 4.53 (m,1), 4.26 (m,2), 3.21 (m,2), 3.11 (m,2), 2.93 (s,3), 2.86 (m,2), 1.91 (m,2), 1.60 (m, 4).

c. 4-(3-Methyl-2-oxoperhydropyrimidin-1-yl)piperidine. Using the procedure of Example 1.j, replacing 1-benzyloxycarbonyl-4-(2-oxo-1,3-oxazolidin-3-yl)piperidine with 1-benzyloxycarbonyl-4-(3-methyl-2-oxoperhydropyrimidin-1-yl)piperidine, the piperidine was obtained as a viscous oil; MS: m/z=198(M+1); NMR (CD$_3$OD): 4.19 (m,1), 3.14 (m,4), 2.98 (m,2), 2.80 (s,3), 2.53 (m,2), 1.82 (m,2), 1.48 (m,4).

EXAMPLE 11

(S)-N-[2-(3,4-Dichlorophenyl)-4-[4-(3-ethyl-2-oxoperhydropyrimidin-1-yl)piperidino]butyl]-N-methylbenzamide citrate Using the procedure of Example 10, replacing 4-(3-methyl-2-oxoperhydropyrimidin-1-yl)piperidine with 4-(3-ethyl-2-oxoperhydropyrimidin-1-yl)piperidine, the title compound was obtained as a white solid; MS: m/z=545(M+1); Analysis for C$_{29}$H$_{38}$Cl$_2$N$_4$O$_2$.1.00 C$_6$H$_8$O$_7$: Calculated: C, 56.98; H, 6.28; N, 7.59. Found: C, 56.66; H, 6.31; N, 7.57.

The intermediate 4-(3-ethyl-2-oxoperhydropyrimidin-1-yl)-piperidine was prepared as follows.

a. 1-Benzyloxycarbonyl-4-(3-ethyl-2-oxoperhydropyrimidin-1-yl)-piperidine. Using the procedure of Example 10.b, replacing iodomethane with iodoethane, the benzyloxycarbonyl compound was obtained as a white solid by trituration with ether; MS: m/z=346(M+1); NMR (CDCl$_3$): 7.34 (m,5), 5.12 (s,2), 4.54 (m,1), 4.26 (m,2), 3.38 (q,2, J=7.1), 3.22 (m,2), 3.11 (m,2), 2.86 (m,2), 1.90 (m,2), 1.60 (m,4), 1.10 (t,3, J=7.1).

b. 4-(3-Ethyl-2-oxoperhydropyrimidin-1-yl)piperidine. Using the procedure of Example 1.j, replacing 1-benzyloxycarbonyl-4-(2-oxo-1,3-oxazolidin-3-yl)piperidine with 1-benzyloxycarbonyl-4-(3-ethyl-2-oxoperhydropyrimidin-1-yl)piperidine, the piperidine was obtained as a viscous oil; MS: m/z=212(M+1); NMR (CDCl$_3$): 4.45 (m,1), 3.38 (q,2, J=7.1), 3.17 (m,6), 2.72 (m,2), 2.15 (m,1), 1.91 (m,2), 1.62 (m,4), 1.10 (t,2, J=7.1).

EXAMPLE 12

(S)-N-[2-(3,4-Dichlorophenyl)-4-[4-[3-(N,N-dimethylcarbamoylmethyl)-2-oxoperhydropyrimidin-1-yl]piperidino]butyl]-N-methylbenzamide citrate Using the procedure of Example 10, replacing 4-(3-methyl-2-oxoperhydropyrimidin-1-yl)piperidine with 4-[3-(N,N-dimethylcarbamoylmethyl)-2-oxoperhydropyrimidin-1-yl]piperidine, the title compound was obtained as a white solid; MS: m/z=602(M+1); Analysis for C$_{31}$H$_{41}$Cl$_2$N$_5$O$_3$.1.10 C$_6$H$_8$O$_7$: Calculated: C, 55.48; H, 6.16; N, 8.60. Found: C, 55.22; H, 6.26; N, 8.65.

The intermediate 4-[3-(N,N- dimethylacetamido)-2-oxoper-hydropyrimidin-1-yl]piperidine was prepared as follows:

a. 1-Benzyloxycarbonyl-4-(3-carboxymethyl-2-oxoperhydropyrimidin-1-yl)piperidine. Potassium tert-butoxide (52 mL, 1 M in tert-butanol) was added to 1-benzyloxycarbonyl-4-(2-oxoperhydropyrimidin-1-yl)piperidine (15.0 g), and the solution was stirred for 35 minutes. tert-Butyl bromoacetate (7.65 mL) was then added, and the mixture was stirred overnight. The reaction mixture was diluted with tetrahydrofuran (20 mL) and dichloromethane (10 mL) followed by the addition of tetrabutylammonium iodide (1.74 g), potassium tert-butoxide (52 mL, 1 M in tert-butanol), and tert-butyl bromoacetate (7.65 mL). After being stirred overnight, the reaction mixture was diluted with dichloromethane and washed with water. The separated organic layer was dried, evaporated to an oil, and dissolved in 1 N hydrochloric acid (700 mL), tetrahydrofuran (200 mL), and methanol (200 mL). After being stirred overnight, the reaction mixture was concentrated in vacuo to remove the organic solvents. The resulting aqueous solution was extracted with dichloromethane, acidified with 2 N hydrochloric acid to a pH of 2, and extracted with dichloromethane. The first organic extract was concentrated to give unreacted 1-benzyloxycarbonyl-4-(2-oxoperhydropyrimidin-1-yl)piperidine (7.0 g). The second organic extract was washed with water, dried, and evaporated. The crude product was triturated from ether and filtered to give the title compound as a white solid (8.3 g); MS: m/z=376(M+1); NMR (CDCl$_3$): 7.35 (m,5), 5.12 (s,2), 4.48 (m,1), 4.28 (m,2), 4.02 (s,2), 3.35 (m,2), 3.18 (m,2), 2.87 (m,2), 1.97 (m,2), 1.65 (m,4).

b. 1-Benzyloxycarbonyl-4-[3-(N,N- dimethylcarbamoylmethyl)-2-oxoperhydropyrimidin-1-yl]piperidine. A solution of 1-benzyloxycarbonyl-4-(3-carboxymethyl-2-oxoperhydropyrimidin-1-yl)-piperidine (2.00 g), dimethylamine hydrochloride (0.522 g), triethylamine (0.89 mL), 4-dimethylaminopyridine (0.781 g), and 1-(3-dimethylaminopropyl)-3-ethylcarbodiimide hydrochloride (1.23 g) in dichloromethane (55 mL) was stirred overnight. The reaction mixture was washed (1 N hydrochloric acid, aqueous sodium bicarbonate), dried, and evaporated. The crude product was chromatographed, with dichloromethane:methanol (gradient 98:2, 80:20) as eluent, triturated from ether, and filtered to give the amide as a white solid (2.00 g); MS: m/z=403(M+1); NMR (CDCl$_3$): 7.35 (m,5), 5.12 (s,2), 4.50 (m,1), 4.27 (m,2), 4.12 (m,2), 3.35 (m,2), 3.18 (m,2), 3.01 (s,3), 2.95 (s,3), 2.84 (m,2), 1.98 (m,2), 1.64 (m,4).

c. 4-[3-(N,N-Dimethylacetamido)- 2-oxoperhydropyrimidin-1-yl]-piperidine. Using the procedure of Example 1.j, replacing 1-benzyloxycarbonyl-4-(2-oxo-1,3-oxazolidin-3-yl)piperidine with 1-benzyloxycarbonyl-4-[3-(N,N-dimethylcarbamoylmethyl)-2-oxoperhydropyrimidin-1-yl]piperidine, the piperidine was obtained as a white solid by trituration from ether; MS: m/z=269(M+1); NMR (CDCl$_3$): 4.40 (m,1), 4.12 (s,2), 3.35 (m,2), 3.24 (m,2), 3.11 (m,2), 3.02 (s,3), 2.95 (s,3), 2.69 (m,2), 2.14 (m,1), 1.98 (m,2) 1.64 (m,4).

EXAMPLE 13

(S)-N-[2-(3,4-Dichlorophenyl)-
4-[4-[3-(N-methylcarbamoyl-methyl)-
2-oxoperhydropyrimidin-1-yl]piperidino]butyl]-
N-methylbenzamide citrate Using the procedure of Example 10, replacing 4-(3-methyl-2-oxoperhydropyrimidin-1-yl)piperidine with 4-[3-(N-methylcarbamoyl-methyl)-2-oxoperhydropyrimidin-1-yl]piperidine, the title compound was obtained as a white solid; MS: m/z=588(M+1); Analysis for $C_{30}H_{39}Cl_2N_5O_3.1.10\ C_6H_8O_7.0.40\ H_2O$: Calculated: C, 54.46; H, 6.06 ; N, 8.67. Found: C, 54.49; H, 6.10; N, 8.64.

The intermediate 4-[3-(N- methylcarbamoylmethyl)-2-oxoper-hydropyrimidin-1-yl]-piperidine was prepared as follows.

a. 1-Benzyloxycarbonyl-4-[3-(N- methylacetamido)-2-oxoperhydropyrimidin-1-yl]piperidine. Using the procedure of Example 12.b, replacing dimethylamine hydrochloride with methylamine hydrochloride, the amide was obtained as a gum; MS: m/z=389(M+1); NMR (CDCl$_3$): 7.35 (m,5), 6.59 (m,1), 5.12 (s,2), 4.47 (m,1), 4.28 (m,2), 3.92 (s,2) 3.34 (m,2), 3.16 (m,2), 2.86 (m,2), 2.80 (s,1.5), 2.79 (s,1.5), 1.96 (m,2), 1.63 (m,4).

b. 4-[3-(N-Methylcarbamoylmethyl)- 2-oxoperhydropyrimidin-1-yl]-piperidine. Using the procedure of Example 1.j, replacing 1-benzyloxycarbonyl-4-(2-oxo-1,3-oxazolidin-3-yl)piperidine with 1-benzyloxycarbonyl- 4-[3-(N-methylcarbamoylmethyl)-2-oxoperhydropyrimidin-1-yl]piperidine, the piperidine was obtained as a gum; MS: m/z=255(M+1); NMR (CDCl$_3$): 6.70 (m,1), 4.38 (m,1), 3.92 (s,2), 3.35 (m,2), 3.23 (m,2), 3.14 (m,2), 2.81 (s,1.5), 2.79 (s,1.5), 2.72 (m,2), 2.10 (m,1), 1.97 (m,2), 1.64 (m,4).

EXAMPLE 14

(S)-N-[2-(3,4-Dichlorophenyl)-
4-[4-[3-(N-benzylcarbamoyl-methyl)-
2-oxoperhydropyrimidin-1-yl]piperidino]butyl]-N-methyl-benzamide citrate.

Using the procedure of Example 10, replacing 4-(3-methyl-2-oxoperhydropyrimidin-1-yl)piperidine with 4-[3-(N-benzylcarbamoyl-methyl)-2-oxoperhydropyrimidin-1-yl]piperidine, the title compound was obtained as a white solid; MS: m/z=664(M+1); Analysis for $C_{36}H_{43}Cl_2N_5O_3.1.10\ C_6H_8O_7.0.60\ H_2O$: Calculated: C, 57.69; H, 6.02; N, 7.89. Found: C, 57.65; H, 6.00; N, 7.90.

The intermediate 4-[3-(N- benzylcarbamoylmethyl)-2-oxoper-hydropyrimidin-1-yl]-piperidine was prepared as follows:

a. 1-Benzyloxycarbonyl-4-[3-(N-benzylcarbamoylmethyl)-2-oxoperhydropyrimidin-1-yl]piperidine. Using the procedure of Example 12.b, replacing dimethylamine hydrochloride with benzylamine and omitting triethylamine, the amide was obtained as a gum; MS: m/z=465(M+1); NMR (CD$_3$OD): 7.34 (m,5), 7.28 (m,5), 5.10 (s,2), 4.38 (s,2), 4.33 (m,1), 4.22 (m,2), 3.99 (s,2), 3.30 (m,2), 3.20 (m,2), 2.85 (m,2), 1.95 (m,2), 1.60 (m,4).

b. 4-[3-(N-Benzylcarbamoylmethyl)- 2-oxoperhydropyrimidin-1-yl]-piperidine. Using the procedure of Example 1.j, replacing 1-benzyloxycarbonyl-4-(2-oxo-1,3-oxazolidin-3-yl)piperidine with 1-benzyloxycarbonyl-4-[3-(N-benzylcarbamoylmethyl)-2-oxoperhydropyrimidin-1-yl]piperidine; the piperidine was obtained as a viscous oil; MS: m/z=331(M+1); NMR (CD$_3$OD): 7.29 (m,5), 4.39 (s,2), 4.30 (m,1), 4.00 (s,2), 3.30 (m,4), 3.16 (m,2), 2.73 (m,2), 1.98 (m,2), 1.68 (m,4).

EXAMPLE 15

(S)-N-[2-(3,4-Dichlorophenyl)-
4-[4-[3-(ethoxycarbonyl-methyl)-2-oxoperhydropyrimidin-1-yl]piperidino]butyl]-N-methyl-benzamide citrate Using the procedure of Example 10, replacing 4-(3-methyl-2-oxoperhydropyrimidin-1-yl)piperidine with 4-[3-(ethoxycarbonylmethyl)-2-oxoperhydropyrimidin-1-yl]piperidine, the title compound was obtained as a white solid; MS: m/z=603(M+1); Analysis for $C_{31}H_{40}Cl_2N_4O_4.1.10\ C_6H_8O_7$: Calculated: C, 55.41; H, 6.04; N, 6.88. Found: C, 55.28; H, 6.11; N, 6.86.

The intermediate 4-[3-(ethoxycarbonylmethyl)-2-oxoper-hydropyrimidin-1-yl]piperidine was prepared as follows.

a. 1-Benzyloxycarbonyl-4-[3-(ethoxycarbonylmethyl)-2-oxoperhydropyrimidin-1-yl]piperidine. A solution of 1-benzyloxycarbonyl-4-(3-carboxymethyl-2-oxoperhydropyrimidin-1-yl)-piperidine (1.51 g), 2-ethoxy-1-ethoxycarbonyl-1,2-dihydroquinoline (1.64 g), and ammonium bicarbonate (1.43 g) in chloroform (30 mL) was stirred for 4 hours. The reaction mixture was diluted with dichloromethane, washed with 1 N hydrochloric acid (5 times), dried, and evaporated. The crude product was chromatographed, with dichloromethane:methanol (gradient 98:2, 90:10) as eluent, and triturated from ether to give the ester as a white solid (1.25 g); MS: m/z=404(M+1); NMR (CDCl$_3$): 7.34 (m,5), 5.11 (s,2), 4.49 (m,1), 4.26 (m,2), 4.18 (q,2, J=7.1), 4.06 (s,2), 3.31 (m,2), 3.17 (m,2), 2.84 (m,2), 1.97 (m,2), 1.64 (m,4), 1.26 (t,3, J=7.1).

b. 4-[3-(Ethoxycarbonylmethyl)-2-oxoperhydropyrimidin-1-yl]-piperidine. Using the procedure of Example 1.j, replacing 1-benzyloxycarbonyl-4-(2-oxo-1,3-oxazolidin-3-yl)piperidine with 1-benzyloxycarbonyl-4-[3-(ethoxycarbonylmethyl)-2-oxoperhydropyrimidin-1-yl]piperidine, the piperidine was obtained as a viscous oil; MS: m/z=270(M+1); NMR (CDCl$_3$): 4.41 (m,1), 4.19 (q,2, J=7.1), 4.07 (s,2), 3.32 (m,2), 3.24 (m,2), 3.12 (m,2), 2.70 (m,2), 2.09 (m,1), 1.98 (m,2), 1.63 (m,4), 1.27 (t,3, J=7.1).

EXAMPLE 16

(S)-N-[2-(3,4-Dichlorophenyl)-
4-[4-(2-oxoperhydropyrimidin-1-yl)piperidino]butyl]-N-ethylbenzamide citrate Using the procedure of Example 10, replacing 4-(3-methyl-2-oxoperhydropyrimidin-1-yl)piperidine with 4-(2-oxoperhydropyrimidin-1-yl)piperidine and N-[2-(3,4-dichlorophenyl)-4-oxobutyl]-N-methyl-benzamide with (S)-N-[2-(3,4-dichlorophenyl)-4-oxobutyl]-N-ethylbenzamide, the title compound was obtained as a white solid; MS: m/z=531(M+1); Analysis for $C_{28}H_{36}Cl_2N_4O_2.1.10\ C_6H_8O_7.0.30\ H_2O$: Calculated: C, 55.53; H, 6.11; N, 7.48. Found: C, 55.51; H, 6.19; N, 7.47.

The intermediate (S)-N-[2-(3,4-dichlorophenyl)- 4-oxobutyl]-N-ethylbenzamide was prepared as follows.

a. (S)-N-[2-(3,4-Dichlorophenyl)-4-hydroxybutyl]benzamide. Benzoic anhydride (14.6 g) in dichloromethane (50 mL) was added dropwise to a solution of (S)-2-(3,4- dichlorophenyl)-4-hydroxy-butylamine (15.0 g) and triethylamine (9.0 mL) in dichloromethane (200 mL) at 0° C. After being stirred at 0° C. for 1 hour and then at ambient temperature for 1 hour, the reaction mixture was washed (1 N hydrochloric acid, saturated aqueous sodium bicarbonate), and the separated organic phase was dried and evaporated. The crude product was chromatographed, with dichloromethane/methanol (gradient 98:2, 90:10) as eluent, to give the amide as a light yellow gum (17.5 g); MS: m/z=338(M+1); NMR (CDCl$_3$): 7.65 (m,2), 7.48 (m,1), 7.38 (m,3), 7.33 (d,1, J=2.1), 7.07 (dd,1, J=2.1, 8.2), 6.44 (m,1,NH), 3.83 (m,1), 3.70 (m,1), 3.58–3.41 (m,2), 3.13 (m,1), 2.47 (m,1, OH), 1.99 (m,1), 1.84 (m,1).

b. (S)-N-[4-Acetoxy-2-(3,4- dichlorophenyl)butyl]benzamide. Acetyl chloride (4.6 mL) was added dropwise to a solution of (S)-N-[2-(3,4-dichlorophenyl)-4- hydroxybutyl]benzamide (17.5 g) and pyridine (8.4 mL) in dichloromethane (400 mL) at 0° C. After being stirred overnight at room temperature, the reaction mixture was washed (water, saturated aqueous copper(II) sulfate), and the separated organic phase was dried and evaporated to give the acetyl-compound as a light yellow oil; MS: m/z=380 (M+1); NMR (CDCl$_3$): 7.63 (m,2), 7.48 (m,1), 7.39 (m,3), 7.32 (d,1, J=2.1), 7.06 (dd,1, J=2.1, 8.2), 6.21 (m,1), 4.03 (m,1), 3.87 (m,2), 3.41 (m,1), 3.07 (m,1), 2.09 (m,1), 1.98 (s,3), 1.92 (m,1).

c. (S)-N-[4-Acetoxy-2-(3,4-dichlorophenyl)butyl]-N- ethylbenzamide. (S)-N-[4-Acetoxy-2-(3,4- dichlorophenyl)butyl]-benzamide (4.2 g) in tetrahydrofuran (15 mL) was cannulated into a suspension of sodium hydride (0.58 g, 60% dispersion in mineral oil) and iodomethane (1.0 mL) in tetrahydrofuran (5 mL). After being stirred overnight, the reaction mixture was concentrated in vacuo, dissolved in dichloromethane, and washed with water. The separated organic layer was dried, evaporated, and chromatographed, with dichloromethane:ether (10:1) as eluent;to give the N-ethyl compound as an oil (3.7 g); MS: m/z=408(M+1).

d. (S)-N-[2-(3,4-Dichlorophenyl)-4-hydroxybutyl]-N-ethyl-benzamide. A solution of (S)-N-[4-acetoxy-2-(3,4-dichlorophenyl)-butyl]-N-ethylbenzamide (3.7 g) in 1 N sodium hydroxide (27 mL), tetrahydrofuran (70 mL), water (20 mL), and methanol (15 mL) was stirred for 3 hours. The reaction mixture was concentrated in vacuo, dissolved in dichloromethane, and washed with water. The separated organic layer was dried and evaporated to give the alcohol as an oil (3.2 g); MS: m/z=366(M+1).

e. (S)-N-[2-(3,4-Dichlorophenyl)-4-oxobutyl]-N-ethylbenzamide. To a solution of oxalyl chloride (1.3 mL) in dichloromethane (30 mL) at −78° C. was added dimethylsulfoxide (2.1 mL) in dichloromethane (10 mL), followed by (S)-N-[2-(3,4-dichlorophenyl)-4-hydroxybutyl]-N-ethylbenzamide (3.2 g) in dichloromethane (15 mL) within 5 minutes. After 15 minutes, triethylamine (8.2 mL) was added, and the reaction mixture was allowed to warm to ambient temperature. The mixture was diluted with dichloromethane, and washed with dilute aqueous hydrochloric acid, water, and aqueous sodium bicarbonate. The separated organic layer was dried, evaporated, and chromatographed, with dichloromethane:ether:hexane (2:1:1) as eluent, to give the tldehyde as an oil (2.5 g); MS: m/z=364(M+1).

EXAMPLE 17

(S)-N-[2-(3,4-Dichlorophenyl)-4-[4-(2-oxoperhydropyrimidin-1-yl)piperidino]butyl]-4-fluoro-N-methylbenzamide citrate 4-Fluorobenzoyl chloride (0.115 mL) was added to a solution of (S)-N-[2-(3,4-dichlorophenyl)- 4-[4-(2-oxoperhydropyrimidin-1-yl)piperidino]butyl]-N-methylamine (0.400 g) and pyridine (0.16 mL) in dichloromethane (10 mL) at −30° C. The reaction mixture was allowed to warm to ambient temperature and stirred for 1 hour. The mixture was diluted with dichloromethane, washed (aqueous sodium bicarbonate, saturated aqueous copper(II) sulfate), dried, and evaporated. The crude product was chromatographed, with dichloromethane:methanol (gradient 98:2, 80:10) as eluent. The purified product (0.350 g) and citric acid (0.126 g) were dissolved in methanol and evaporated to give the title compound as a glass which was scraped out as a white solid (0.450 g); MS: m/z=535(M+1); Analysis for $C_{27}H_{33}Cl_2FN_4O_2 \cdot 1.10\ C_6H_8O_7 \cdot 0.10\ (C_2H_5)_2O \cdot 0.70\ H_2O$: Calculated: C, 53.25; H, 5.80; N, 7.30. Found: C, 53.22; H, 5.70; N, 7.30.

The intermediate (S)-N-[2-(3,4-dichlorophenyl)- 4-[4-(2-oxoperhydropyrimidin-1-yl)piperidino]butyl]-N-methylamine was prepared as follows:

a. tert-Butyl (S)-N-[2-(3,4-dichlorophenyl)- 4-hydroxybutyl]-N-methylcarbamate. Di-tert-butyl dicarbonate (21.6 g) in dichloromethane (125 mL) was added dropwise to a solution of (S)-N-methyl-2-(3,4- dichlorophenyl)-4-hydroxybutylamine (25.0 g) in dichloromethane (125 mL) over a period of 30 minutes. After being stirred for 3 hours, the reaction mixture was washed (0.1 N hydrochloric acid, aqueous sodium bicarbonate), dried, and evaporated. The crude product was chromatographed, with dichloromethane:ether (2:1) as eluent, to give the tert-butyl ester as an oil (33.0 g) that crystallized upon standing.

b. tert-Butyl (S)-N-[2-(3,4-dichlorophenyl)-4-oxobutyl]-N-methylcarbamate. Using the procedure of Example 16.e, replacing (S)-N-[2-(3,4-dichlorophenyl)- 4-hydroxybutyl]-N-ethylbenzamide with tert-Butyl (S)-N-[2-(3,4-dichlorophenyl)-4-hydroxybutyl]-N-methyl-carbamate, the aldehyde was obtained as an oil that was used crude in the following reaction.

c. tert-Butyl (S)-N-[2-(3,4-dichlorophenyl)- 4-[4-(2-oxoperhydropyrimidin-1-yl)piperidino]butyl]-N-methylcarbamate. Using the procedure of Example 10, replacing 4-(3-methyl-2-oxoperhydropyrimidin-1-yl)piperidine with 4-(2-oxoperhydropyrimidin-1-yl)-piperidine and N-[2-(3,4-dichlorophenyl)-4-oxobutyl]-N-methylbenzamide with tert-Butyl (S)-N-[2-(3,4-dichlorophenyl)-4-oxobutyl]-N-methylcarbamate, the title compound was obtained as a gum.

d. (S)-N-[2-(3,4-Dichlorophenyl)- 4-[4-(2-oxoperhydropyrimidin-1-yl)piperidino]butyl]-N-methylamine. Trifluoroacetic acid (7.5 mL) was added to a solution of tert-butyl (S)-N-[2-(3,4-dichlorophenyl)-4-[4- (2-oxoperhydropyrimidin-1-yl)piperidino]butyl]-N-methylcarbamate (5.1 g) in dichloromethane (200 mL). After 30 minutes, additional trifluoroacetic acid (7.5 mL) was added, and the reaction mixture was stirred for 4 hours. The mixture was washed with 1 N sodium hydroxide (250 mL), dried, and evaporated to give the title compound as a gum (3.8 g); MS: m/z=413(M+1).

EXAMPLE 18

(S)-N-[2-(3,4-Dichlorophenyl)-
4-[4-(2-oxoperhydropyrimidin-1-yl)piperidino]bu-
tyl]-4-methyl-N-methylbenzamide citrate Using a procedure similar to that described in Example 17, except replacing 4-fluorobenzoyl chloride with p-toluoyl chloride, the title compound was obtained as a white solid; MS: m/z=531(M+1); Analysis for $C_{28}H_{36}Cl_2N_4O_3 \cdot 1.10$ $C_6H_8O_7 \cdot 0.10$ $H_2O$: $(C_2H_5)_2O \cdot 0.30$ $H_2O$: Calculated: C, 55.63; H, 6.18; N, 7.41. Found: C, 55.58; H, 6.17; N, 7.52.

EXAMPLE 19

(S)-N-[2-(3,4-Dichlorophenyl)-
4-[4-(2-oxoperhydropyrimidin-1-yl)piperidino]bu-
tyl]-4-methoxy-N-methylbenzamide citrate Using the same procedure as Example 17, replacing 4-fluorobenzoyl chloride with 4-methoxybenzoyl chloride, the title compound was obtained as a white solid; MS: m/z=547(M+1); Analysis for $C_{28}H_{36}Cl_2N_4O_4 \cdot 1.10$ $C_6H_8O_7 \cdot 0.10$ $(C_2H_5)_2O \cdot 0.70$ $H_2O$: Calculated: C, 53.92; H, 6.10; N, 7.19. Found: C, 53.93; H, 5.99; N, 7.19.

EXAMPLE 20

(S)-N-[2-(3,4-Dichlorophenyl)-
4-[4-(2-oxoperhydropyrimidin-1-yl)piperidino]bu-
tyl]-4-hydroxy-N-methylbenzamide citrate A solution of (S)-N-[2-(3,4-dichlorophenyl)- 4-[4-(2-oxoperhydropyrimidin-1-yl)piperidino]butyl]-N-methylamine (1.22 g), 4-acetoxybenzoic acid (0.640 g), and 1-(3-dimethylaminopropyl)-3-ethylcarbodiimide hydrochloride (0.682 g) in dichloromethane (30 mL) was stirred overnight. The reaction mixture was diluted with dichloromethane, washed (water, aqueous sodium bicarbonate), dried, and evaporated. The crude product was chromatographed twice, with dichloromethane:methanol (gradient 95:5, 80:20) as eluent. The purified product (0.190 g) and citric acid (0.069 g) were dissolved in methanol and evaporated to give the title compound as a glass which was scraped out as a white solid (0.220 g); MS: m/z=533(M+1); Analysis for $C_{27}H_{34}Cl_2N_4O_3 \cdot 1.10$ $C_6H_8O_7 \cdot 0.60$ $H_2O$: Calculated: C, 53.40; H, 5.86; N, 7.41. Found: C, 53.45; H, 6.13; N, 7.26.

EXAMPLE 21

1-[(S)-N-Benzoyl-3-(3,4-dichlorophenyl)-
N-methyl-4-aminobutyl]-
4-(2-oxoperhydropyrimidin-1-yl)piperidine 1-oxide 3-Chloroperoxybenzoic acid (0.700 g) in dichloromethane (16 mL) was added dropwise to a solution of (S)-N-[2-(3,4-dichlorophenyl)-4-[4-(2-oxoperhydropyrimidin-1-yl)piperidino]butyl]-N-methylbenzamide (1.31 g) in dichloromethane (12 mL) at 0° C. After being stirred for 1 hour, the reaction mixture was diluted with dichloromethane, washed with aqueous sodium bicarbonate, dried, and evaporated. The crude product was chromatographed, with dichloromethane:methanol (gradient 98:2, 70:30) as eluent. The purified product (0.592 g) and p-toluenesulfonic acid monohydrate (0.232 g) were dissolved in dichloromethane:methanol and evaporated to give the title compound as a white solid (0.824 g); MS: m/z=533(M+1); Analysis for $C_{27}H_{34}Cl_2N_4O_3 \cdot 1.10$ $C_7H_8O_3 \cdot 1.10$ $H_2O$: Calculated: C, 56.11; H, 6.10; N, 7.54. Found: C, 55.85; H, 5.96; N, 7.33.

EXAMPLE 22

N-[2-(3,4-Dichlorophenyl)-4-[4-(3-methyl-
2-oxo-imidazolidin-1-yl)piperidino]butyl]-
N-methylbenzamide hydrochloride To a suspension of sodium hydride (30 mg, 60% dispersion in oil) in tetrahydrofuran (1 mL) was added N-[2-(3,4-dichlorophenyl)-4-[4-(2-oxoimidazolidin-1-yl)piperidino]butyl]-N-methylbenzamide (152 mg) in tetrahydrofuron (2 mL). After 30 minutes, iodomethane (0.021 mL) was added, and the reaction mixture was stirred for 2.5 hours. The mixture was diluted with dichloromethane and washed with water. The separated organic layer was dried and evaporated to an oil, which was dissolved in a minimum amount of dichloromethane and precipitated out with ethereal hydrogen chloride. The solvent was evaporated to an off white solid (104 mg); MS: m/z=517(M+1); Analysis for $C_{27}H_{34}N_4O_2Cl_2 \cdot 1.2$ $HCl \cdot 0.1$ $(C_2H_5)_2O$: Calculated: C, 57.83; H, 6.42; N, 10.05. Found: C, 57.85; H, 6.41; N, 9.85.

The intermediate N-[2-(3,4-dichlorophenyl)- 4-[4-(2-oxoimidazolidin-1-yl)piperidino]butyl]-N-methylbenzamide was prepared using a sequence similar to that described in Example 3 and the sub-parts thereof by substituting N-[-2-(3,4-dichlorophenyl)-4-oxobutyl]-N-methylbenzamide for the (S)-N-[-2-(3,4-dichlorophenyl)-4-oxobutyl]-N-methylbenzamide used in sub-part 3.d.

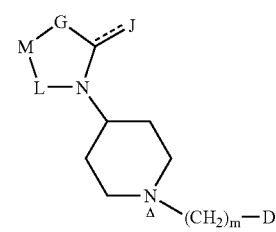

I

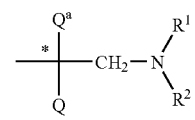

Ia

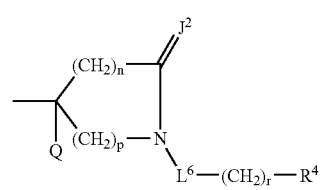

Ib

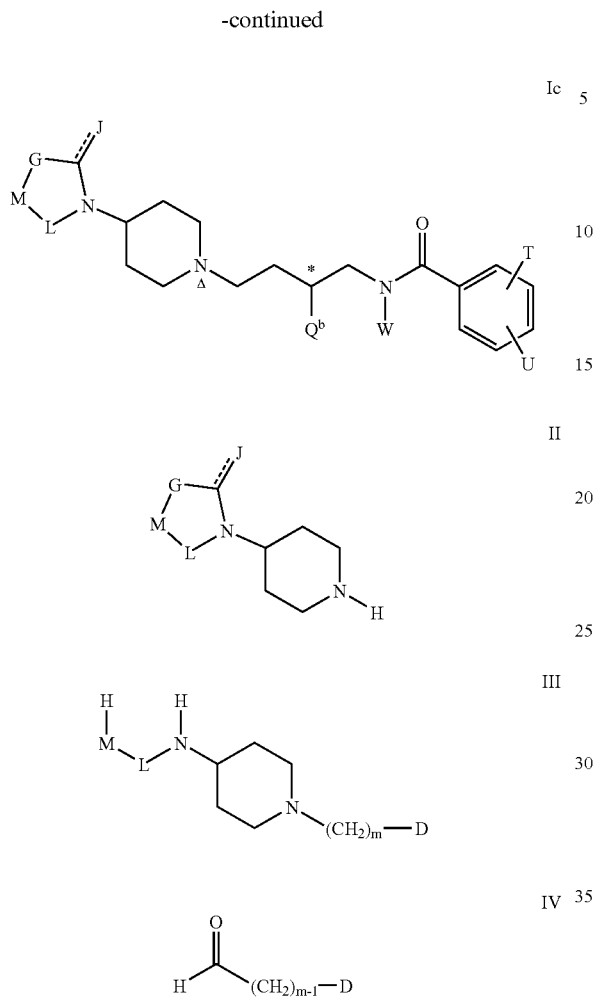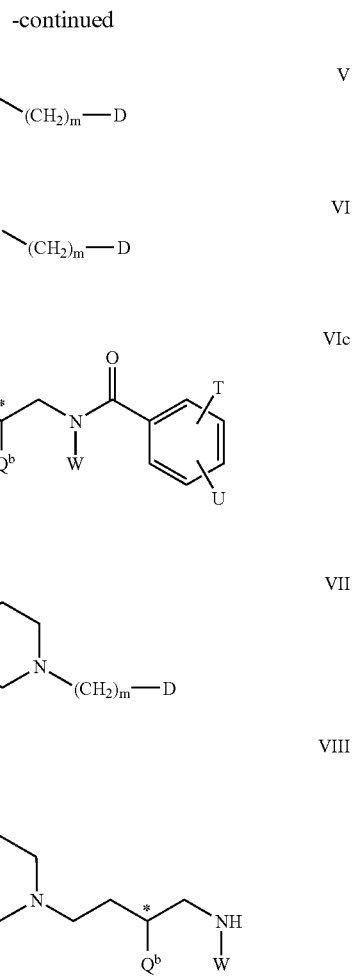

The invention claimed is:
1. A compound made by a process comprising:
a) reductively alkylating 4-oxopiperidine under mild acid conditions with an aldehyde of formula IV

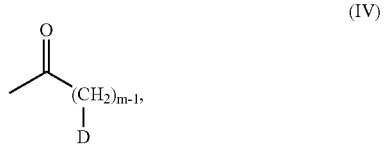

wherein D is a residue of formula Ia or formula Ib

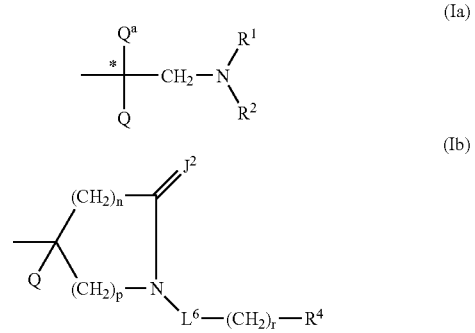

wherein
Q is phenyl which may have one or two substituents independently selected from halo, trifluoromethyl, hydroxy, $(C_{1-3})$alkoxy, $(C_{1-3})$alkyl and methylenedioxy; or
Q is thienyl, imidazolyl, benzo[b]thiophenyl or naphthyl any of which may have a halo substituent; or
Q is biphenylyl; or
Q is carbon-linked indolyl which may have a benzyl substituent at the 1-position;
$Q^a$ is hydrogen, $(C_{1-4})$alkyl, or a radical of formula $-(CH^2)q-NR^5R^6$ in which q is 2 or 3 and $R^5$ and $R^6$ are independently $(C_{1-4})$alkyl or $NR^5R^6$ is piperidino or 4-benzylpiperidino;
$R^1$ is hydrogen, methyl or $(C_{2-6})$n-alkyl which may have a terminal amino radical;
$R^2$ is $-C(=O)R^3$, $-C(=O)OR^3$ or $-C(=J^1)NHR^3$ in which $J^1$ is oxygen or sulfur and $R^3$ is hydrogen, $(C_{1-4})$alkyl, phenyl$(C_{1-3})$alkyl (which phenyl may have one or more substituents selected from halo, hydroxy, $(C_{1-4})$alkoxy or $(C_{1-4})$alkyl), pyridyl$(C_{1-3})$alkyl, naphthyl$(C_{1-3})$alkyl, pyridylthio$(C_{1-3})$alkyl, styryl, 1-methylimidazol-2-ylthio$(C_{1-3})$alkyl, aryl (which may have one or more substituents selected from halo, hydroxy, $(C_{1-4})$alkoxy or $(C_{1-4})$alkyl), heteroaryl (which may have one or more halo, hydroxy, $(C_{1-4})$alkoxy or $(C_{1-4})$alkyl substituents), or may be α-hydroxybenzyl when $R^2$ is $-COR^3$;
n is 0, 1, 2 or 3;
$J^2$ is oxygen or two hydrogens;
p is 1 or 2, and when p is 2, n is 1 and $J^2$ is two hydrogens;
$L^6$ is carbonyl or methylene;
r is 0, 1, 2, or 3;
$R^4$ is phenyl which may have one or more substituents selected from halo, trifluoromethyl, $(C_{1-4})$alkyl, hydroxy or $(C_{1-4})$alkoxy; naphthyl which may have one or more substituents selected from halo, trifluoromethyl, $(C_{1-4})$alkyl or hydroxy; pyridyl; thienyl; indolyl; quinolinyl; benzothienyl or imidazolyl; or when $L^6$ is carbonyl, the group $-(CH_2)r-R^4$ may be aryl, heteroaryl or a benzyl group having an α-substituent selected from hydroxy, $(C_{1-4})$alkoxy and $(C_{1-4})$alkyl, and further wherein the aryl, heteroaryl or phenyl portion of the benzyl group may have one or more substituents selected independently from halo, trifluoromethyl, $(C_{1-4})$alkyl, hydroxy and $(C_{1-4})$alkyl, hydroxy and $(C_{1-4})$alkoxy;
G denotes a single bond, a double bond or a divalent hydrocarbon radical;
J denotes a radical joined to the ring by a single bond if G denotes a double bond or, otherwise, a radical joined by a double bond, and
m is 2 or 3;
followed by reduction with sodium cyanoborohydride in an alcoholic solvent, or, alkylating said piperidine with an alkylating agent of formula V

wherein Y is a leaving group selected from iodide, bromide, methanesulfonate, p-toluenesulfonate, trifluoromethanesulfonate, or the like, to form a piperidone of formula VII

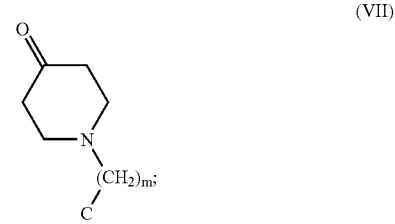

b) reductively alkylating said piperidone of formula VII with an amine of formula HM-L-NH$_2$ wherein:
M denotes a heteroatom or substituted heteroatom; and
L denotes a hydrocarbon radical in which the 1-position is attached to M; wherein
the values of G, J, M and L in combination are selected from
(a) G is a single bond; J is oxo or thioxo; M is oxy, thio or NR$^{12}$; and L is L$^1$;
(b) G is a single bond; J is NR$^8$; M is NR$^7$; and L is L$^1$;
(c) G is a double bond, J is OR$^7$, SR$^7$ or NR$^9$R$^{10}$; M is nitrogen; and L is L$^1$;
(d) G is methylene which may have one or two methyl substituents; J is oxo, thio or NR$^{11}$; M is oxy, thio, sulfinyl, sulfonyl or NR$^7$; and L is L$^2$;
(e) G is a single bond; J is oxo, thioxo or NR$^{11}$; M is nitrogen; and L is L$^3$;
(f) G is methine, which may have a (1–3C)alkyl substituent; J is oxo, thioxo or NR$^{11}$; M is nitrogen; and L is L$^4$; and
(g) G is cis-vinylene, which may have one or two methyl substituents; J is oxo, thioxo, or NR$^{11}$; M is nitrogen; and L is L$^5$; wherein $R^7$ is hydrogen or $(C_{1-3})$alkyl;

$R^8$ is hydrogen, $(C_{1-3})$alkyl, cyano, $(C_{1-3})$alkylsulfonyl or nitro;

$R^9$ and $R^{10}$ are independently hydrogen or $(C_{1-3})$alkyl or the radical $NR^9R^{10}$ is pyrrolidino, piperidino, morpholino, thiomorpholino or its S-oxide, or piperazino which may have a $(C_{1-3})$alkyl substituent at the 4-position;

$R^{11}$ is hydrogen or $(C_{1-3})$alkyl;

$R^{12}$ is hydrogen, $(C_{1-3})$alkyl, RaOC(=O)CH$_2$— or RbRcNC(=O)CH$_2$—;

Ra is hydrogen or $(C_{1-3})$alkyl;

Rb and Rc are independently hydrogen, $(C_{1-3})$alkyl, phenyl or benzyl;

$L^1$ is ethylene, cis-vinylene, trimethylene or tetramethylene which radical $L^1$ itself may have one or two methyl substituents;

$L^2$ is ethylene or trimethylene which radical $L^2$ itself may have one or two methyl substituents;

$L^3$ is prop-2-en-1-yliden-3-yl, which radical $L^3$ itself may have one or two methyl substituents;

$L^4$ is cis-vinylene, which radical $L^4$ itself may have one or two methyl substituents; and $L^5$ is methine, which radical $L^5$ itself may have a $(C_{1-3})$alkyl substituent;

to form an amine of formula III

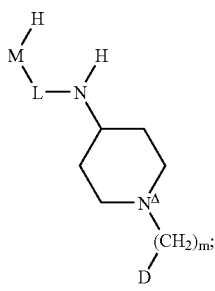

(III)

c) cyclizing said amine by reacting it with a diactivated carbonic acid derivative selected from 1,1'-carbonyldiimidazole, chloroformate esters selected from methyl, ethyl or phenyl esters, and carbonate diesters selected from phosgene, diphosgene and triphosgene; or with a diactivated thiocarbonyl derivative selected from 1,1'-thiocarbonyldi-2(1H)-pyridone, 1,1'-thiocarbonyldiimidazole, phenyl chlorodithioformate and thiophosgene; said cyclization being carried in an inert solvent, selected from chloroform, tetrahydrofuran or toluene, at a temperature from about ambient temperature to the reflux temperature of the reaction mixture, and d) forming a pharmaceutically-acceptable salt or an N-oxide of said compound; selected from N-[2-(3,4-dichlorophenyl)-4-[4-(2-oxo-1,3-oxazolidin-3-yl)piperidino]butyl]-N-methylbenzamide;

(S)-N-[2-(3,4-dichlorophenyl)-4-(2-oxoperhydro-1,3-oxazin-3-yl)piperidino]butyl]-N-methylbenzamide;

(S)-N-[2-(3,4-dichlorophenyl)-4-[4-(2-oxoimidazolidin-1-yl)piperidino]butyl]-N-methylbenzamide;

(S)-N-[2-(3,4-dichlorophenyl)-4-[4-(2-thioxoimidazolidin-1-yl)piperidino]butyl]-N-methylbenzamide;

(S)-N-[2-(3,4-dichlorophenyl)-4-[4-(2-oxoperhydropyrimidin-1-yl)piperidino]butyl]-N-methylbenzamide;

(S)-N-[2-(3,4-dichlorophenyl)-4-[4-(2-thioxoperhydropyrimidin-1-yl)piperidino]butyl]-N-methylbenzamide;

(S)-N-[2-(3,4-dichlorophenyl)-4-[4-(3-methyl-2-thioxoperhydropyrimidin-1-yl)piperidino]butyl]-N-methylbenzamide;

(S)-N-[2-(3,4-dichlorophenyl)-4-[4-(2-oxo-1,3-perhydrodiazepin-1-yl)piperidino]butyl]-N-methylbenzamide;

(S)-N-[2-(3,4-dichlorophenyl)-4-[4-(2-oxo-5,5-dimethylperhydropyrimidin-1-yl)piperidino]butyl]-N-methylbenzamide;

(S)-N-[2-(3,4-dichlorophenyl)-4-[4-(3-methyl-2-oxoperhydropyrimidin-1-yl)piperidino]butyl]-N-methylbenzamide;

(S)-N-[2-(3,4-dichlorophenyl)-4-[4-(3-ethyl-2-oxoperhydropyrimidin-1-yl)piperidino]butyl]-N-methylbenzamide;

(S)-N-[2-(3,4-dichlorophenyl)-4-[4-[3-(N,N-dimethylcarbamoylmethyl)-2-oxoperhydropyrimidin-1-yl)piperidino]butyl]-N-methylbenzamide;

(S)-N-[2-(3,4-dichlorophenyl)-4-[4-[3-(N-methylcarbamoyl-methyl)-2-oxoperhydropyrimidin-1-yl]piperidino]butyl]-N-methylbenzamide;

(S)-N-[2-(3,4-dichlorophenyl)-4-[4-[3-(N-benzylcarbamoyl-methyl)-2-oxoperhydropyrimidin-1-yl]piperidino]butyl]-N-methyl-benzamide;

(S)-N-[2-(3,4-dichlorophenyl)4-[4-[3-(ethoxycarbonylmethyl)-2-oxoperhydropyrimidin-1-yl]piperidino]butyl]-N-methylbenzamide;

(S)-N-[2-(3,4-dichlorophenyl)-4-[4-2-oxoperhydropyrimidin-1-yl)piperidino]butyl]-N-ethylbenzamide;

(S)-N-[2-(3,4-dichlorophenyl)-4-[4-2-oxoperhydropyrimidin-1-yl)piperidino]butyl]-4-fluoro-N-methylbenzamide;

(S)-N-[2-(3,4-dichlorophenyl)-4-[4-2-oxoperhydropyrimidin-1-yl)piperidino]butyl]-4-methyl-N-methylbenzamide;

(S)-N-[2-(3,4-dichlorophenyl)-4-[4-2-oxoperhydropyrimidin-1-yl)piperidino]butyl]-4-methoxy-N-methylbenzamide;

(S)-N-[2-(3,4-dichlorophenyl)-4-[4-2-oxoperhydropyrimidin-1-yl)piperidino]butyl]-4-hydroxy-N-methylbenzamide;

1-[(S)-N-benzoyl-3-(3,4-dichlorophenyl)-N-methyl-4-aminobutyl]-4-(2-oxoperhydropyrimidin-1-yl)piperidine 1-oxide, or N-[2-(3,4-dichlorophenyl)-4-[4-(3-methyl-2-oxo-imidazolidin-1-yl)piperidino]butyl]-N-methylbenzamide, or a pharmaceutically-acceptable salt or an N-oxide of a foregoing compound.

2. A compound made by the process of claim 1 wherein said compound is selected from:

N-[2-(3,4-dichlorophenyl)-4-[4-(2-oxo-1,3-oxazolidin-3-yl)piperidino]butyl]-N-methylbenzamide;

(S)-N-[2-(3,4-dichlorophenyl)-4-[4-(2-oxoimidazolidin-1-yl)piperidino]butyl]-N-methylbenzamide;

(S)-N-[2-(3,4-dichlorophenyl)-1)-4-[4-(2-thioxoimidazolidin-1-yl)piperidino]butyl]-N-methylbenzamide;

N-[2-(3,4-dichlorophenyl)-4-[4-(3-methyl-2-oxo-imidazolidin-1-yl)piperidino]butyl]-N-methylbenzamide, or a pharmaceutically-acceptable salt or an N-oxide of a foregoing compound.

3. A compound made by the process of claim 1, wherein said compound is selected from:

(S)-N-[2-(3,4-dichlorophenyl)-4-[4- (2-oxoperhydropyrimidin-1-yl)piperidino]butyl]-N-methylbenzamide;

(S)-N-[2-(3,4-dichlorophenyl)-4-[4- (2-thioxoperhydropyrimidin-1-yl)piperidino]butyl]-N-methylbenzamide;

(S)-N-[2-(3,4-dichlorophenyl)-4-[4- (3-methyl-2-thioxoperhydropyrimidin-1-yl)piperidino]butyl]-N-methylbenzamide;

(S)-N-[2-(3,4-dichlorophenyl)-4-[4- (2-oxo-5,5-dimethylperhydropyrimidin-1-yl)piperidino]butyl]-N-methylbenzamide;

(S)-N-[2-(3,4-dichlorophenyl)-4-[4- (3-methyl-2-oxoperhydropyrimidin-1-yl)piperidino]butyl]-N-methylbenzamide;

(S)-N-[2-(3,4-dichlorophenyl)-4-[4- (3-ethyl-2-oxoperhydropyrimidin-1-yl)piperidino]butyl]-N-methylbenzamide;

(S)-N-[2-(3,4-dichlorophenyl)-4-[4-[3-(N,N-dimethylcarbamoylmethyl)-2- oxoperhydropyrimidin-1-yl]piperidino]butyl]-N-methylbenzamide;

(S)-N-[2-(3,4-dichlorophenyl)-4-[4-[3-(N- methylcarbamoyl-methyl)-2-oxoperhydropyrimidin-1yl]piperidino]butyl]-N-methylbenzamide;

(S)-N-[2-(3,4-dichlorophenyl)-4-[4-[3-(N- benzylcarbamoyl-methyl)-2-oxoperhydropyrimidin-1yl]piperidino]butyl]-N-methylbenzamide;

(S)-N-[2-(3,4-dichlorophenyl)-4-[4-[3- (ethoxycarbonylmethyl)-2-oxoperhydropyrimidin-1-1yl]piperidino]butyl]-N-methylbenzamide;

(S)-N-[2-(3,4-dichlorophenyl)-4-[4-(2- oxoperhydropyrimidin-1-yl)piperidino]butyl]-N-ethylbenzamide;

(S)-N-[2-(3,4-dichlorophenyl)-4-[4-(2- oxoperhydropyrimidin-1-yl)piperidino]butyl]-4-fluoro-N-methylbenzamide;

(S)-N-[2-(3,4-dichlorophenyl)-4-[4-(2- oxoperhydropyrimidin-1-yl)piperidino]butyl]methyl-N-methylbenzamide;

(S)-N-[2-(3,4-dichlorophenyl)-4-[4-(2- oxoperhydropyrimidin-1-yl)piperidino]butyl]methoxy-N-methylbenzamide;

(S)-N-[2-(3,4-dichlorophenyl)-4-[4-(2- oxoperhydropyrimidin-1-yl)piperidino]butyl]hydroxy-N-methylbenzamide, or 1-[(S)-N- benzoyl-3-(3,4-dichlorophenyl)-N-methyl-4-aminobutyl]-4- (2-oxoperhydropyrimidin-1-yl)piperidine 1-oxide, or a pharmaceutically-acceptable salt or an N-oxide of a foregoing compound.

* * * * *

SEQUENCE LISTING
```
<160> NUMBER OF SEQ ID NOS: 2
<210> SEQ ID NO 1
<211> LENGTH: 15
<212> TYPE: DNA
<213> ORGANISM: Artificial
<220> FEATURE:
<223> OTHER INFORMATION: Synthetic
<400> SEQUENCE: 1
gcgcaagctt atggg                                                    15
<210> SEQ ID NO 2
<211> LENGTH: 18
<212> TYPE: DNA
<213> ORGANISM: artificial
<220> FEATURE:
<223> OTHER INFORMATION: Synthetic
<400> SEQUENCE: 2
gtccccataa gcttgcgc                                                 18
```